US012802367B2

(12) United States Patent
Kanno et al.

(10) Patent No.: US 12,802,367 B2
(45) Date of Patent: Nov. 17, 2026

(54) ASSISTANCE SYSTEM, ASSISTANCE DEVICE, AND ASSISTED DEVICE

(71) Applicant: RIVERFIELD Inc., Tokyo (JP)

(72) Inventors: Takahiro Kanno, Tokyo (JP); Naoto Shono, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 119 days.

(21) Appl. No.: 18/773,737

(22) Filed: Jul. 16, 2024

(65) Prior Publication Data

US 2024/0371118 A1 Nov. 7, 2024

Related U.S. Application Data

(63) Continuation of application No. PCT/JP2022/005123, filed on Feb. 9, 2022.

(51) Int. Cl.
*G06T 19/00* (2011.01)
*A61B 90/00* (2016.01)
(Continued)

(52) U.S. Cl.
CPC ............ *G06T 19/006* (2013.01); *A61B 90/37* (2016.02); *G06F 3/011* (2013.01); *G06F 3/1454* (2013.01); *G09B 5/02* (2013.01); *G06T 2210/41* (2013.01); *G06T 2219/004* (2013.01); *G06T 2219/024* (2013.01)

(58) Field of Classification Search
None
See application file for complete search history.

(56) References Cited

U.S. PATENT DOCUMENTS

2006/0125846 A1* 6/2006 Springer .................. G09B 5/02 345/629
2007/0274704 A1* 11/2007 Nakajima .............. G06V 10/17 396/310
(Continued)

FOREIGN PATENT DOCUMENTS

JP 2000-271147 A 10/2000
JP 2013-510672 A 3/2013
(Continued)

OTHER PUBLICATIONS

Office Action dated Jan. 14, 2026 issued in U.S. Appl. No. 18/773,703.
(Continued)

*Primary Examiner* — Joni Hsu
(74) *Attorney, Agent, or Firm* — Sughrue Mion, PLLC

(57) ABSTRACT

An assistance system includes an assisted device and an assistance device disposed to be separated from the assisted device. The assistance device includes a three-dimensional position detector that three-dimensionally detects a hand position of an instructor, and a data transmitter that transmits position information indicating the hand position detected by the three-dimensional position detector. The assisted device includes a first image generator that generates a three-dimensional hand model image imitating a hand of the instructor based on the transmitted position information, and a first image combiner that combines the hand model image with a captured image taken by the assisted device to generate a first combined image.

17 Claims, 15 Drawing Sheets

(51) Int. Cl.

| | |
|---|---|
| ***G06F 3/01*** | (2006.01) |
| ***G06F 3/14*** | (2006.01) |
| ***G09B 5/02*** | (2006.01) |

(56) References Cited

U.S. PATENT DOCUMENTS

| | | | | |
|---|---|---|---|---|
| 2011/0118752 | A1 | 5/2011 | Itkowitz et al. | |
| 2012/0045742 | A1* | 2/2012 | Meglan | G09B 23/303 434/268 |
| 2012/0235990 | A1* | 9/2012 | Yamaji | H04N 13/225 345/419 |
| 2015/0049163 | A1* | 2/2015 | Smurro | H04L 65/403 348/14.08 |
| 2015/0102979 | A1* | 4/2015 | Ikuta | G09G 3/34 345/1.3 |
| 2016/0306421 | A1* | 10/2016 | Piccinini | G06F 3/015 |
| 2016/0358383 | A1* | 12/2016 | Gauglitz | G06F 3/0304 |
| 2017/0026638 | A1* | 1/2017 | Harris | H04N 13/327 |
| 2018/0285636 | A1* | 10/2018 | Fei | G02B 27/017 |
| 2021/0015343 | A1 | 1/2021 | Uyama et al. | |
| 2021/0072947 | A1* | 3/2021 | Anderson | G06F 3/011 |
| 2021/0393343 | A1 | 12/2021 | Sankai | |
| 2022/0079705 | A1 | 3/2022 | Navkar et al. | |
| 2023/0222740 | A1 | 7/2023 | Katsuki et al. | |
| 2024/0187560 | A1 | 6/2024 | Goto | |

FOREIGN PATENT DOCUMENTS

| | | | |
|---|---|---|---|
| JP | 2019-162339 | A | 9/2019 |
| WO | 2019/083805 | A1 | 5/2019 |
| WO | 2021/176091 | A1 | 9/2021 |

OTHER PUBLICATIONS

Communication dated Apr. 24, 2026 issued by the United States Patent and Trademark Office in U.S. Appl. No. 18/773,703.

* cited by examiner

ASSISTANCE SYSTEM, ASSISTANCE DEVICE, AND ASSISTED DEVICE

CROSS-REFERENCE TO RELATED APPLICATION

This Application is a continuation of International Patent Application No. PCT/JP2022/005123, filed on Feb. 9, 2022, in the Japan Patent Office, the contents of which being incorporated by reference herein in their entirety.

BACKGROUND

The present disclosure relates to a technique for an instructor to give instruction to a surgical operator from a remote location.

An assistance system may allow a surgical operator to perform a surgical operation on a patient while receiving instructions of an instructor at a remote location. This assistance system is used when, for example, a less experienced operation doctor (the surgical operator) performs surgery while receiving instruction of an experienced instruction doctor (the instructor).

SUMMARY

It is an aspect to provide an assistance system with which an instructor at a remote location can appropriately assist a surgical operator.

According to an aspect of one or more embodiments, there is provided an assistance system comprising an assisted device; and an assistance device disposed to be separated from the assisted device. The assistance device includes a first storage that stores one or more first programs and a first central processing unit (CPU), and the first CPU accesses the first storage and executes the one or more first programs to cause the first CPU to implement a three-dimensional position detecting unit that three-dimensionally detects a hand position of an instructor; and a data transmission unit that transmits position information indicating the hand position detected by the three-dimensional position detecting unit. The assisted device includes a second storage that stores one or more second programs and a second central processing unit (CPU), and the second CPU accesses the first storage and execute the one or more second programs to cause the second CPU to implement a first image generation unit that generates a hand model image in three dimensions that imitates a hand of the instructor based on the transmitted position information; and a first image combining unit that combines the hand model image with a captured image taken by the assisted device to generate a first combined image.

DETAILED DESCRIPTION

Figure 1:
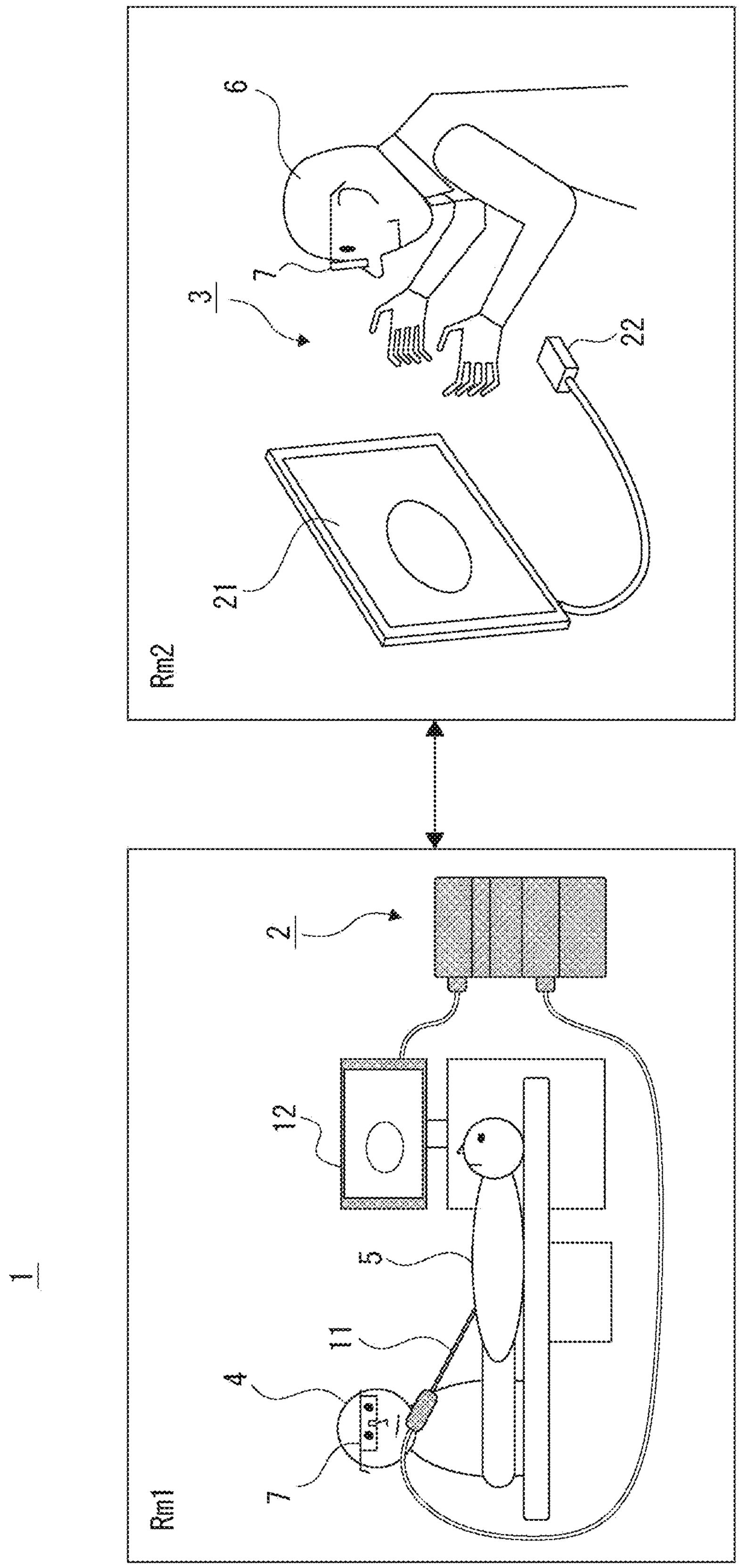
FIG. 1 is a drawing for describing an assistance system, according to an embodiment.

A monitor displaying a captured image (hereinafter also noted as an endoscope image) by an endoscope inserted into a patient may be located at a remote location, and an instructing doctor at the remote location can input instructions while observing the endoscope image displayed on the monitor. Meanwhile, on a monitor on a surgery room side, a combined image in which instruction contents input at the remote location are superimposed on the endoscope image is displayed, and an operation doctor can perform surgery on the patient while receiving the instructions of the instruction doctor at the remote location.

The above-described assistance system allows an instructor to observe captured images displayed on a monitor and to provide instructions. Thus, even a less experienced surgical operator can perform a reliable surgical operation on a patient, and skills of the surgical operator himself/herself can be improved.

When such an assistance system is employed in a field where the safety of a surgical operation subject (a patient) of the above-described endoscopic surgery and the like is required, it may be difficult for a surgical operator to understand instruction contents of an instructor with only display of the instruction contents of the instructor.

Various embodiments herein have been made in consideration of the above-described circumstances, and it is an aspect to provide an assistance system with which an instructor at a remote location can appropriately assist a surgical operator.

An assistance system according to an embodiment may include an assisted device and an assistance device disposed to be separated from the assisted device. The assistance device includes a three-dimensional position detecting unit that three-dimensionally detects a hand position of an instructor, and a data transmission unit that transmits position information indicating the hand position detected by the three-dimensional position detecting unit. The assisted device includes a first image generation unit that generates a three-dimensional hand model image imitating a hand of the instructor based on the transmitted three-dimensional position information, and a first image combining unit that combines the hand model image with a captured image taken by the assisted device to generate a first combined image.

Accordingly, since the assisted device displays the hand model image imitating the hand of the instructor at a remote location, a surgical operator can grasp the move of the hand of the instructor. Therefore, the surgical operator can understand instruction contents of the instructor with more accuracy.

The following describes various embodiments. Each configuration described below merely indicates one example for achieving one or more embodiments. Accordingly, it is possible to make various modifications corresponding to design and the like as long as they are within the scope not departing from the technical idea of the present disclosure. In order to avoid duplication for the configuration that has been described once, hereinafter, identical reference numerals will be given, and the re-description will be omitted for conciseness, in some cases.

[1-1. Outline of Assistance System]

Figure 2:
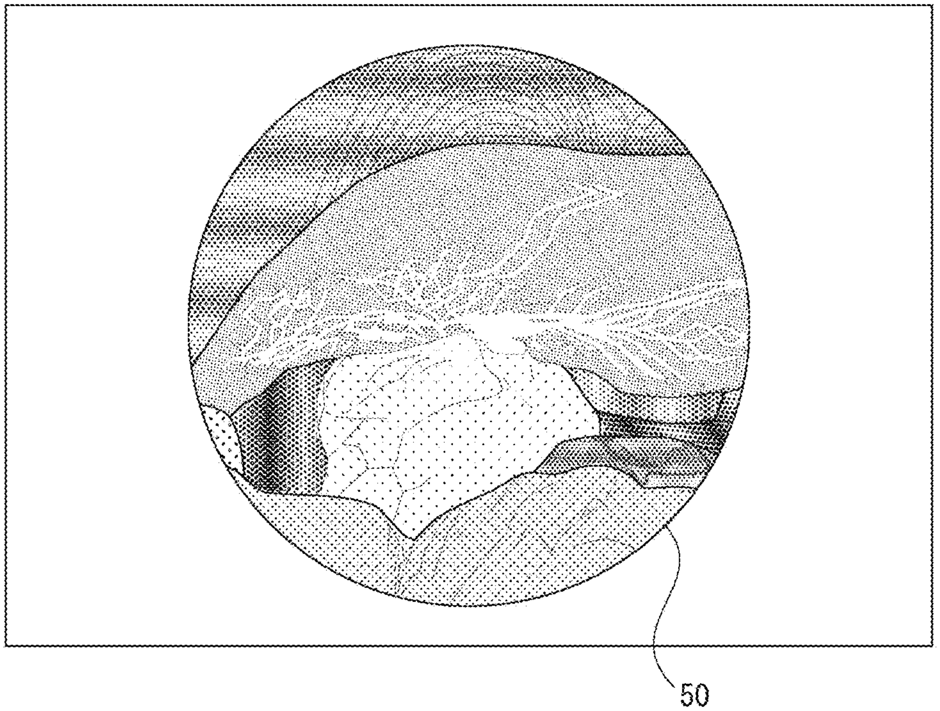
FIG. 2 is a drawing illustrating an endoscope image, according to an embodiment.
Figure 3:
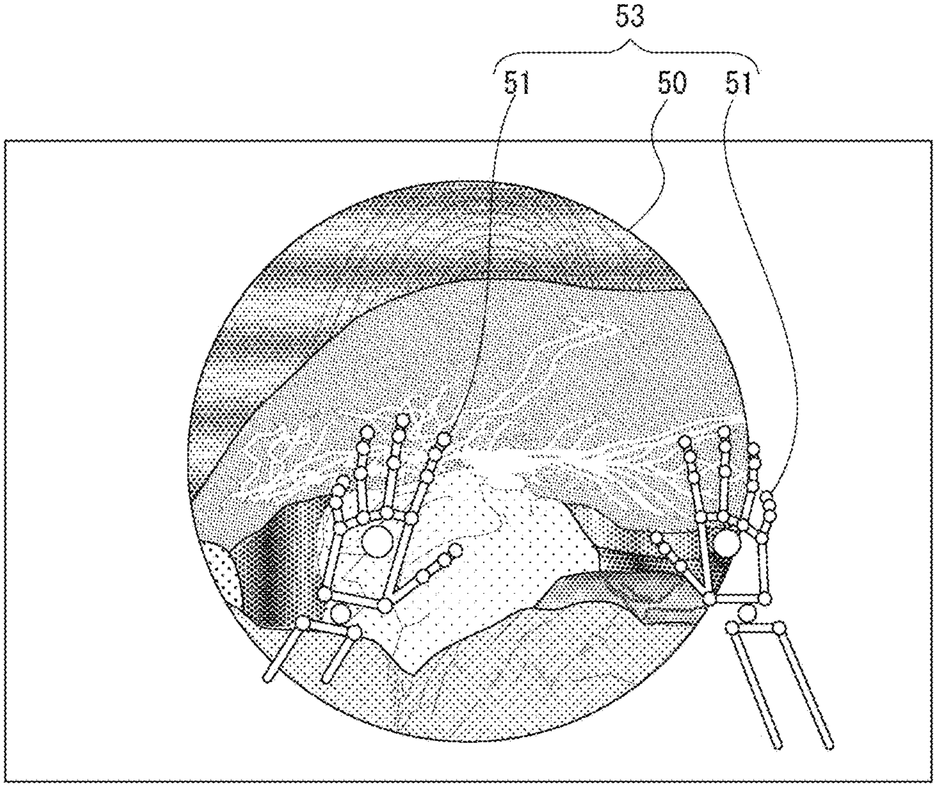
FIG. 3 is a drawing illustrating a combined image in which a hand model image is superimposed on the endoscope image, according to an embodiment.
Figure 4:
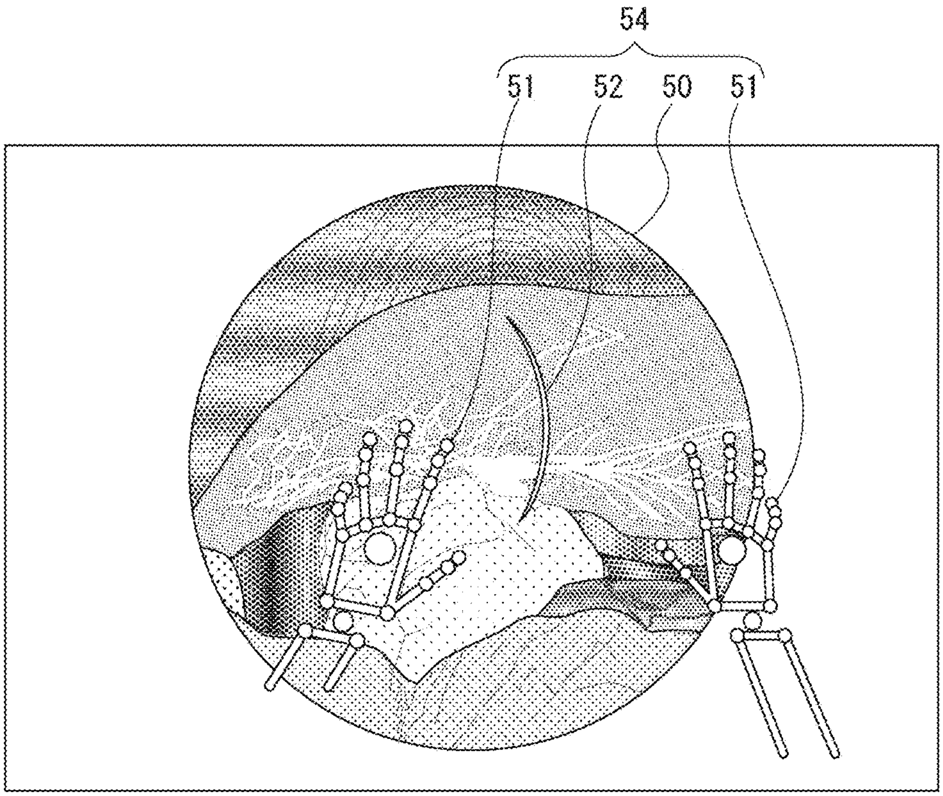
FIG. 4 is a drawing illustrating a combined image in which the hand model image and an annotation image are superimposed on the endoscope image, according to an embodiment.
Figure 5:
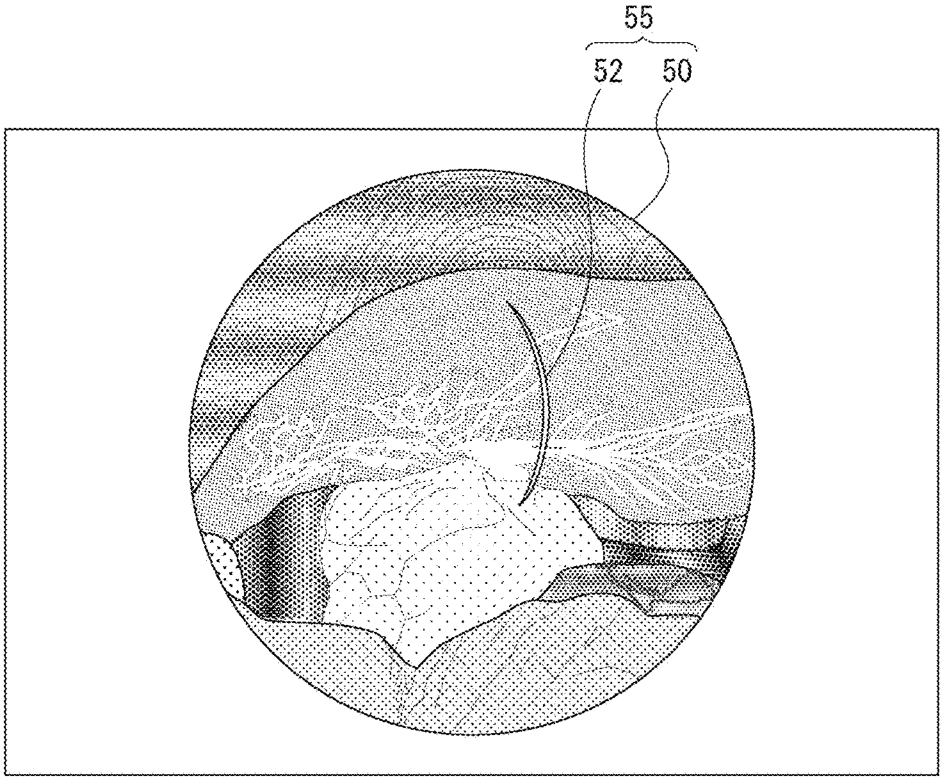
FIG. 5 is a drawing illustrating a combined image in which the annotation image is superimposed on the endoscope image, according to an embodiment.

FIG. 1 is a drawing for describing an assistance system 1, according to an embodiment. FIG. 2 is a drawing illustrating an endoscope image 50, according to an embodiment. FIG. 3 is a drawing illustrating a combined image 53 in which a hand model image 51 is superimposed on the endoscope image 50, according to an embodiment. FIG. 4 is a drawing illustrating a combined image 54 in which the hand model image 51 and an annotation image 52 are superimposed on the endoscope image 50, according to an embodiment. FIG. 5 is a drawing illustrating a combined image 55 in which the annotation image 52 is superimposed on the endoscope image 50, according to an embodiment.

Note that while the hand model image 51 and the annotation image 52 are actually 3D (three-dimensional) images, the hand model image 51 and the annotation image 52 are illustrated as 2D (two-dimensional) images in FIG. 3 to FIG. 5. While the endoscope image 50 may be a 3D image or a 2D image, the endoscope image 50 is illustrated as a 2D image in FIG. 2 to FIG. 5.

As illustrated in FIG. 1, the assistance system 1 includes an operation-side device 2 used by a surgical operator 4 in a surgery room Rm1 and an instruction-side device 3 used by an instructor 6 in an instruction room Rm2 separated from the surgery room Rm1. Accordingly, the operation-side device 2 and the instruction-side device 3 are separately disposed.

For example, it is assumed that the surgical operator 4 is an operation doctor of a patient 5 and the instructor 6 is an instruction doctor who instructs the surgical operator 4, and in the assistance system 1, the surgical operator 4 can perform surgery on the patient 5 while confirming instructions of the instructor 6.

The operation-side device 2 includes an endoscope 11 and a 3D monitor 12. The instruction-side device 3 includes a 3D monitor 21 and a three-dimensional position detecting unit 22.

In the 3D monitor 12 and the 3D monitor 21, polarization filters having different polarization directions between odd-numbered lines (pixel columns in the horizontal direction) and even-numbered lines are alternately stacked on a flat panel, such as a Liquid Crystal Display (LCD), and the 3D monitor 12 and the 3D monitor 21 are monitors that can display a 3D (three-dimensional) image by what is called a line-by-line method.

In the 3D monitor 12 and the 3D monitor 21, for example, right-handed circular polarization filters are stacked on the odd-numbered lines, and left-handed circular polarization filters are stacked on the even-numbered lines.

The surgical operator 4 wears polarized glasses 7 to visually confirm the 3D monitor 12. The polarized glasses 7 include polarization filters having different polarization directions between a right eye side and a left eye side. For example, the polarized glasses 7 include a right-handed circular polarization filter attached to the right eye side and a left-handed circular polarization filter attached to the left eye side.

Accordingly, the surgical operator 4 wearing the polarized glasses 7 can see only an image on the odd-numbered lines by the right eye, and can see only an image on the even-numbered lines by the left eye when visually confirming the 3D monitor 12.

Similarly, when the instructor 6 wears the polarized glasses 7 to visually confirm the 3D monitor 21, the instructor 6 can see only an image on the odd-numbered lines by the right eye, and can see only an image on the even-numbered lines by the left eye.

Thus, the 3D monitor 12 and the 3D monitor 21 show different images for the right eye and the left eye (parallax images) through the polarized glasses 7 to the surgical operator 4 and the instructor 6, respectively, thereby enabling showing a 3D image.

The 3D monitor 12 and the 3D monitor 21 can show also a 2D image to the surgical operator 4 and the instructor 6 by displaying the same image on the odd-numbered lines and the even-numbered lines.

In the assistance system 1, in the operation-side device 2, for example, when the endoscope 11 is inserted into a body cavity of the patient 5, the endoscope image 50 in the body cavity as illustrated in FIG. 2 is displayed on the 3D monitor 12. The surgical operator 4 can confirm the endoscope image 50 on the 3D monitor 12. The endoscope image 50 may be a 3D image, or may be a 2D image.

The endoscope image 50 is displayed also on the 3D monitor 21 of the instruction-side device 3 in the instruction room Rm2. The instructor 6 can confirm the endoscope image 50 on the 3D monitor 21 while staying in the instruction room Rm2.

As described later in detail, the instruction-side device 3 can three-dimensionally detect a position (a coordinate) of a hand of the instructor 6 with the three-dimensional position detecting unit 22. The instruction-side device 3 displays the three-dimensional hand model image 51 imitating the hand of the instructor 6 on the endoscope image 50 based on the position of the hand of the instructor 6 detected by the three-dimensional position detecting unit 22.

That is, the instruction-side device 3 displays the combined image 53 in which the hand model image 51 is superimposed on the endoscope image 50 as illustrated in FIG. 3 on the 3D monitor 21.

Thus, the instructor 6 can input instruction contents while three-dimensionally confirming the move of his/her own hand on the endoscope image 50 with the hand model image 51.

In the instruction-side device 3, the instruction contents can be operationally input by a predetermined move (gesture) of the hand of the instructor 6 detected by the three-dimensional position detecting unit 22. The input causes the instruction-side device 3 to display the annotation image 52 indicating the instruction contents (operation input) of the instructor 6 on the endoscope image 50.

That is, the instruction-side device 3 displays the combined image 54 in which the hand model image 51 and the annotation image 52 are superimposed on the endoscope image 50 as illustrated in FIG. 4 on the 3D monitor 21.

Thus, the instructor 6 can three-dimensionally confirm of his/her own instruction contents on the endoscope image 50 with the annotation image 52.

Meanwhile, the operation-side device 2 displays the combined image 55 in which the annotation image 52 is superimposed on the endoscope image 50, as illustrated in FIG. 5, based on the instruction contents of the instructor 6 on the 3D monitor 12.

Thus, the surgical operator 4 can perform a surgical operation on the patient 5 while three-dimensionally confirming the instruction contents of the instructor 6 displayed on the 3D monitor 12.

[1-2. Configuration of Operation-Side Device 2]

Figure 6:
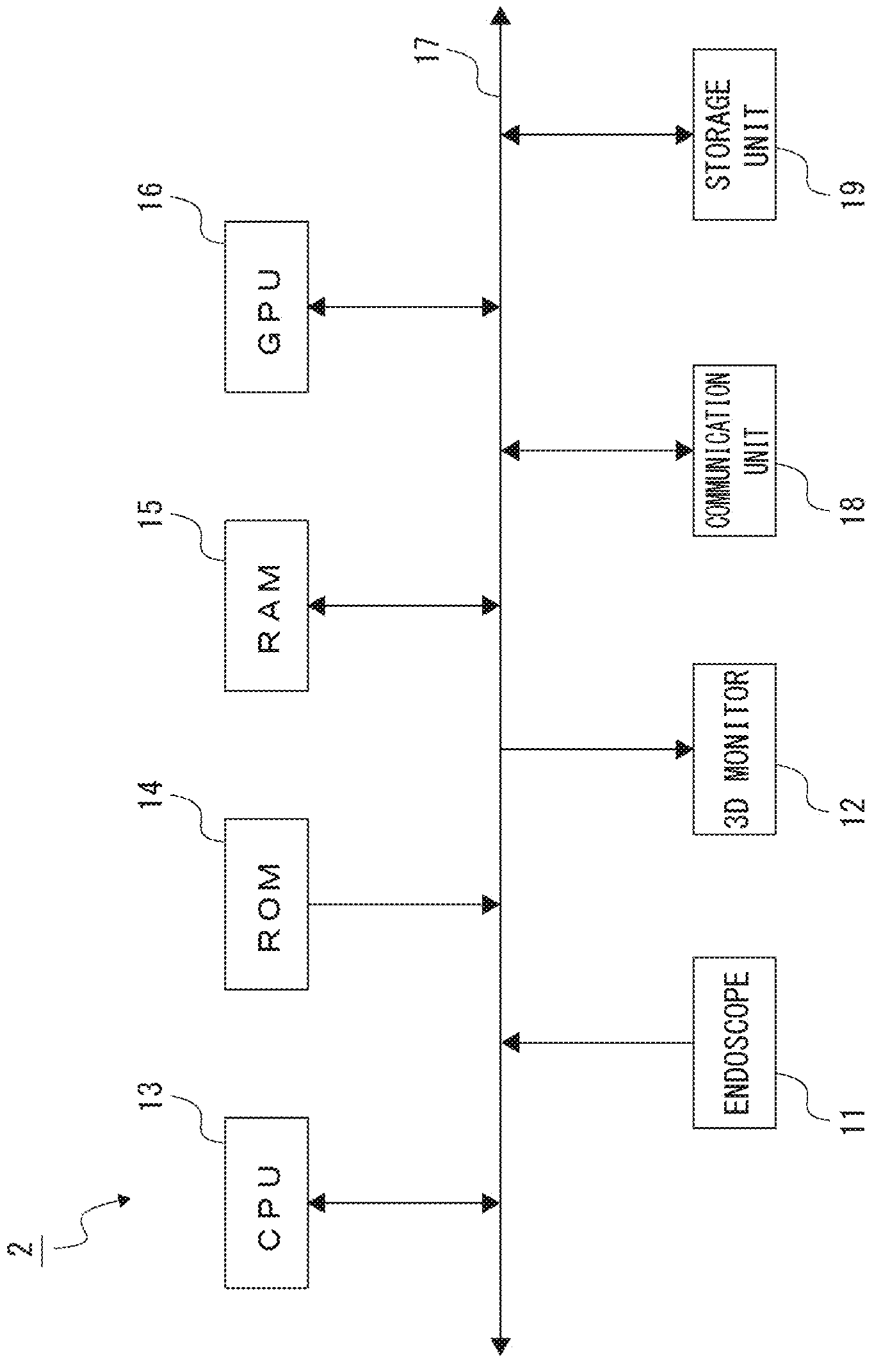
FIG. 6 is a block diagram illustrating an exemplary configuration of an operation-side device, according to an embodiment.

FIG. 6 is a block diagram illustrating an exemplary configuration of the operation-side device 2, according to an embodiment. As illustrated in FIG. 6, the operation-side device 2 has a configuration including a computer provided with a Central Processing Unit (CPU) 13, a Read Only Memory (ROM) 14, a Random Access Memory (RAM) 15, and a Graphics Processing Unit (GPU) 16, in addition to the endoscope 11 and the 3D monitor 12.

The CPU 13 executes various kinds of processing according to programs stored in the ROM 14 and/or a storage unit 19. The RAM 15 stores, for example, data for executing the various kinds of processing by the CPU 13.

The GPU 16 performs a drawing process (for example, a shader process) with 3D computer graphics according to drawing instructions from the CPU 13, and stores an image after the drawing process in a frame buffer (not illustrated). Then, the GPU 16 outputs the image stored in the frame buffer to the 3D monitor 12. The GPU 16 may include a memory storing program code. The GPU 16 accesses the memory and executes the program code to cause the GPU 16 to implement the drawing process.

The CPU 13, the ROM 14, the RAM 15, and the GPU 16 are mutually connected via a bus 17. The endoscope 11, the 3D monitor 12, a communication unit 18, and the storage unit 19 are also connected to the bus 17.

The communication unit 18 performs wired or wireless communication with the instruction-side device 3. The communication unit 18 may be implemented as a communication interface.

The storage unit 19 is configured as a storage, such as a Hard Disk Drive (HDD) and/or a Solid State Drive (SSD). The storage unit 19 can store, for example, various kinds of information. The storage unit 19 can also be used for storing program data to execute the various kinds of processing by the CPU 13.

Figure 7:
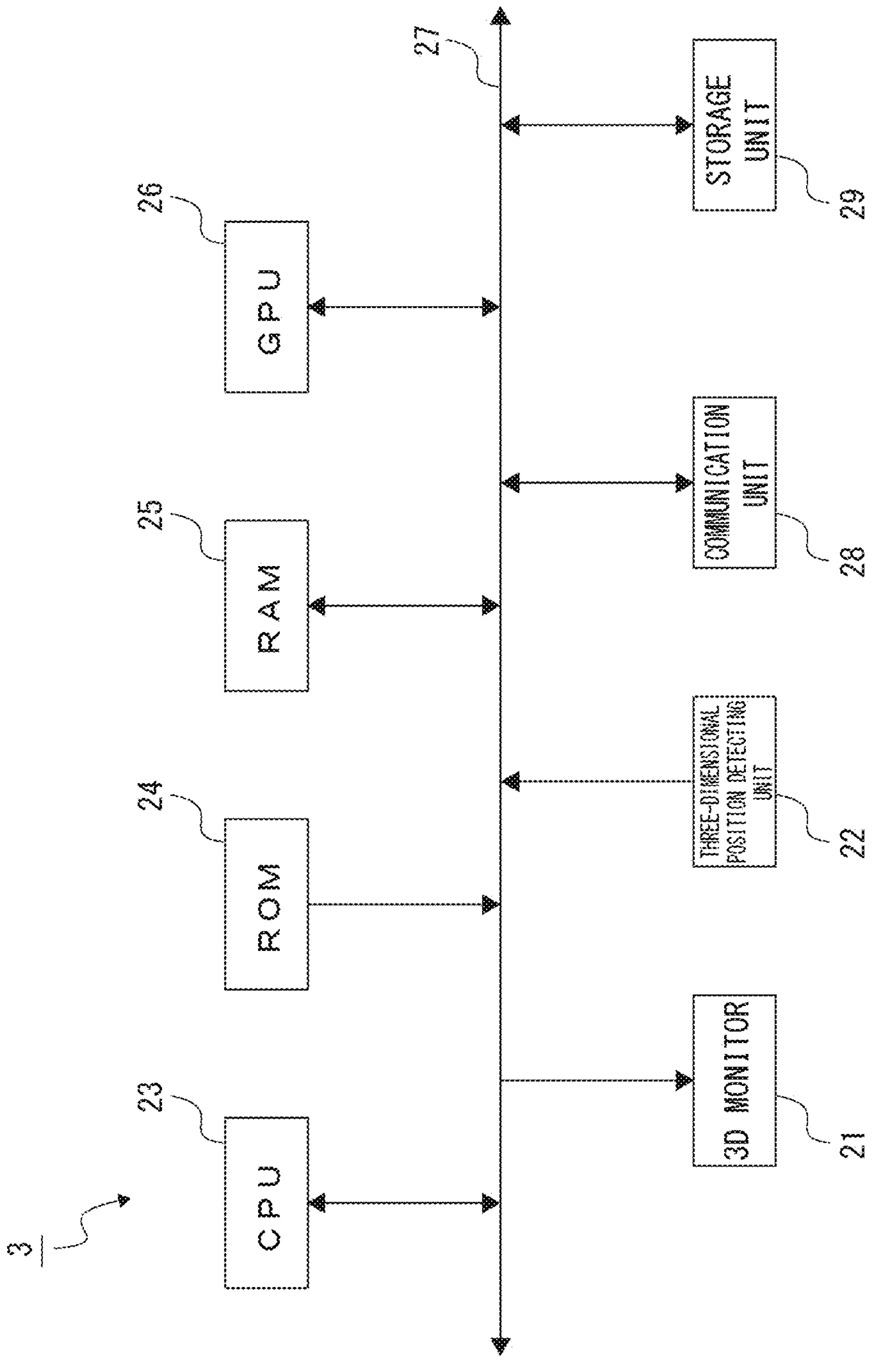
FIG. 7 is a block diagram illustrating an exemplary configuration of an instruction-side device, according to an embodiment.

FIG. 7 is a block diagram illustrating an exemplary configuration of the instruction-side device 3, according to an embodiment. As illustrated in FIG. 7, the instruction-side device 3 has a configuration including a computer provided with a CPU 23, a ROM 24, a RAM 25, a communication unit 28, and a GPU 26, in addition to the 3D monitor 21 and the three-dimensional position detecting unit 22.

The CPU 23 executes various kinds of processing according to programs stored in the ROM 24 or a storage unit 29. The RAM 25 stores, for example, data for executing the various kinds of processing by the CPU 23.

The GPU 26 performs a drawing process (for example, a shader process) with 3D computer graphics according to drawing instructions from the CPU 23, and stores an image after the drawing process in a frame buffer (not illustrated). Then, the GPU 26 outputs the image stored in the frame buffer to the 3D monitor 21. The GPU 16 may include a memory storing program code. The GPU 16 accesses the memory and executes the program code to cause the GPU 16 to implement the drawing process.

The CPU 23, the ROM 24, the RAM 25, and the GPU 26 are mutually connected via a bus 27. The 3D monitor 21, the three-dimensional position detecting unit 22, the communication unit 28, and the storage unit 29 are also connected to the bus 27.

The communication unit 28 performs wired or wireless communication with the operation-side device 2. The communication unit 28 may be implemented as a communication interface.

The storage unit 29 is configured as a storage, such as an HDD and/or an SSD. The storage unit 29 can store, for example, various kinds of information. The storage unit 29 can also be used for storing program data to execute the various kinds of processing by the CPU 23.

Figure 8:
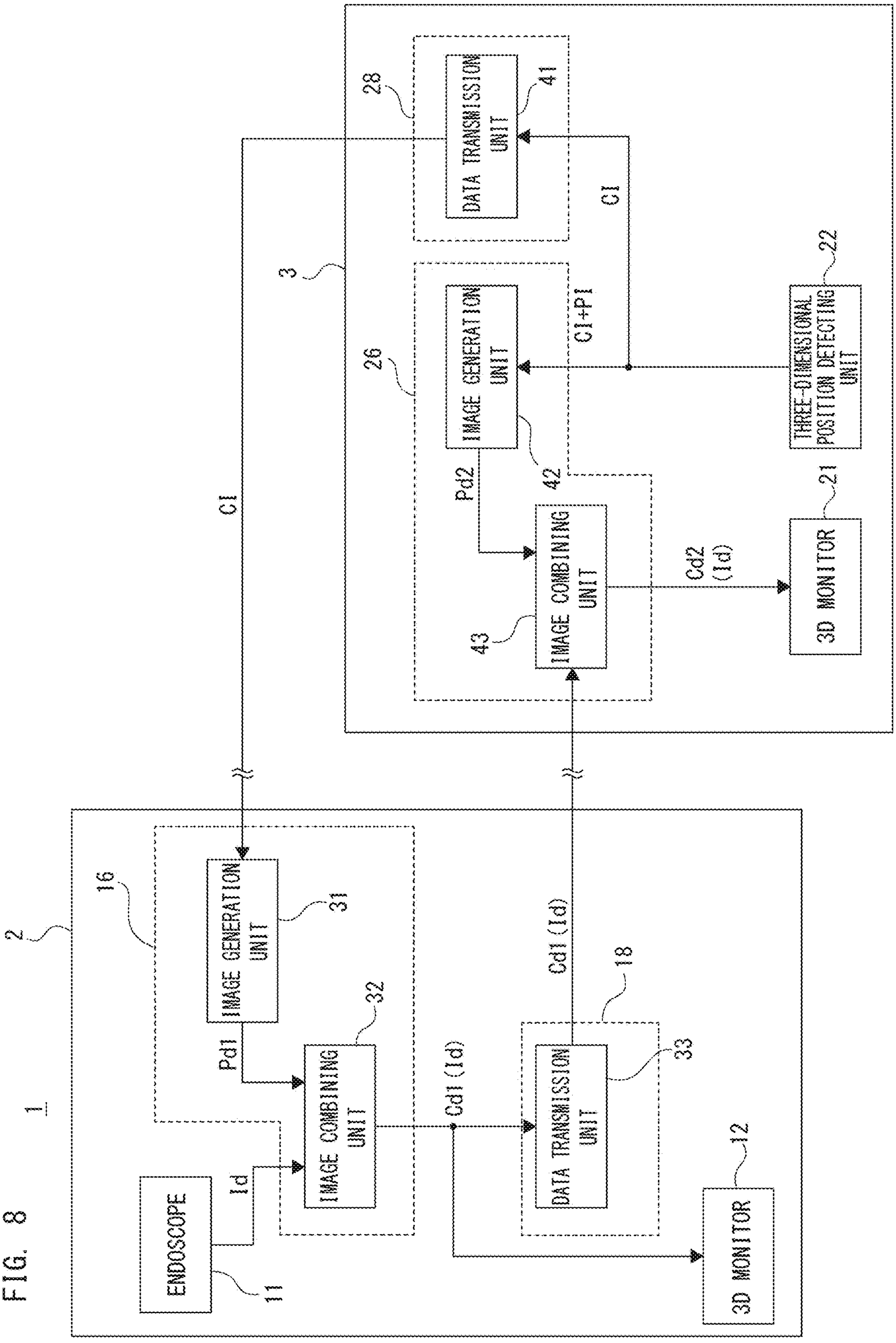
FIG. 8 is a drawing for describing a functional configuration and a flow of data in an assistance system, according to an embodiment.

FIG. 8 is a drawing for describing a functional configuration and a flow of data in the assistance system 1, according to an embodiment. As illustrated in FIG. 8, the GPU 16 of the operation-side device 2 functions as an image generation unit 31 and an image combining unit 32. The communication unit 18 of the operation-side device 2 functions as a data transmission unit 33.

The communication unit 28 of the instruction-side device 3 functions as a data transmission unit 41. The GPU 26 of the instruction-side device 3 functions as an image generation unit 42 and an image combining unit 43.

The endoscope 11 includes an imaging device, generates the endoscope image 50 by performing predetermined signal processing on a captured image signal obtained by the imaging device, and outputs image data of the endoscope image 50 (hereinafter noted as endoscope image data Id) to the image combining unit 32. When the endoscope image 50 is a 3D image, the endoscope 11 includes the two imaging devices, and the two endoscope images 50 (parallax images) are generated based on the captured image signals obtained by the respective imaging devices.

The image generation unit 31 generates the annotation image 52 based on instruction content information CI transmitted from the instruction-side device 3, and outputs image data of the annotation image 52 (hereinafter noted as 3D image data Pd1) to the image combining unit 32.

Here, the instruction content information CI includes information on the coordinate, the line type, the color, the line width, and the like specified by the operation input.

The image combining unit 32 combines images based on the various kinds of input image data. In the embodiment described above with reference to FIGS. 1-5, the image combining unit 32 combines the endoscope image 50 based on the endoscope image data Id with the annotation image 52 based on the 3D image data Pd1 to generate the combined image 55.

Then, the image combining unit 32 outputs image data of the combined image 55 (hereinafter noted as operation-side combined image data Cd1) to the data transmission unit 33 and the 3D monitor 12.

When the 3D image data Pd1 is not input, the image combining unit 32 outputs the endoscope image data Id to the data transmission unit 33 and the 3D monitor 12 without generating the combined image 55.

Accordingly, the 3D monitor 12 performs the display based on the endoscope image data Id and the operation-side combined image data Cd1. That is, the 3D monitor 12 displays the endoscope image 50 and the combined image 55.

The data transmission unit 33 transmits various kinds of data to the instruction-side device 3. For example, the data transmission unit 33 transmits the endoscope image data Id and the operation-side combined image data Cd1 input from the image combining unit 32.

The three-dimensional position detecting unit 22 includes a sensor that three-dimensionally measures the position (the coordinate) of the hand of the instructor 6, and is, for example, Leap Motion Controller manufactured by Ultraleap.

The three-dimensional position detecting unit 22 includes an infrared irradiation unit, a stereo infrared camera, and the like, and photographs a reflected light of an infrared light emitted from the infrared irradiation unit and reflected by the hand of the instructor 6 with the stereo infrared camera to obtain a stereo infrared image.

Then, the three-dimensional position detecting unit 22 performs an image analysis of the obtained stereo infrared image to three-dimensionally detect positions of joints of the hand (fingers, the palm, and the like) and positions of tips of fingers of the instructor 6 (hereinafter, they are simply noted as a hand position of the instructor 6) in a three-dimensional space. The position here is a position indicated by three-dimensional coordinates having a predetermined origin as a reference position.

The three-dimensional position detecting unit 22 three-dimensionally detects the instruction contents of the instructor 6 based on position information PI (operation input). For example, when a gesture in which a tip of a thumb and a tip of a forefinger of the instructor 6 are in contact with each other is detected based on the detected position information PI, the three-dimensional position detecting unit 22 detects a trajectory of the tip of the thumb and the tip of the forefinger moving while being in contact with each other as instruction contents.

The three-dimensional position detecting unit 22 outputs the position information PI indicating the detected hand position of the instructor 6 to the image generation unit 42, and outputs the instruction content information CI indicating the detected instruction contents of the instructor 6 to the image generation unit 42 and the data transmission unit 41.

The data transmission unit 41 transmits various kinds of data to the operation-side device 2. In the embodiment described above with reference to FIGS. 1-5, the data transmission unit 41 transmits the instruction content information CI input from the three-dimensional position detecting unit 22.

The image generation unit 42 generates the hand model image 51 or the hand model image 51 and the annotation image 52 based on the position information PI and the instruction content information CI input from the three-dimensional position detecting unit 22, and outputs image data thereof (hereinafter noted as 3D image data Pd2) to the image combining unit 43.

The image combining unit 43 combines images based on the various kinds of input image data. For example, the image combining unit 43 combines the endoscope image 50 based on the endoscope image data Id with the hand model image 51 or the hand model image 51 and the annotation image 52 based on the 3D image data Pd2 to generate the combined images 53, 54. Then, the image combining unit 43 outputs image data of the generated combined images 53, 54 (hereinafter noted as instruction-side combined image data Cd2) to the 3D monitor 21.

When the 3D image data Pd2 is not input, the image combining unit 43 outputs the endoscope image data Id to the 3D monitor 21 without generating the combined images 53, 54.

Accordingly, the 3D monitor 21 performs the display based on the endoscope image data Id and the instruction-side combined image data Cd2. That is, the 3D monitor 21 displays the endoscope image 50 and the combined images 53, 54.

[1-3. Details of Assistance System 1]

The assistance system 1 will be described in detail with reference to FIG. 8.

First, in the operation-side device 2, the endoscope image data Id obtained by the endoscope 11 is input to the image combining unit 32.

When the 3D image data Pd1 is not input from the image generation unit 31, the image combining unit 32 outputs the endoscope image data Id to the 3D monitor 12 and the data transmission unit 33.

The 3D monitor 12 displays the endoscope image 50 based on the endoscope image data Id (see FIG. 2). This enables the surgical operator 4 to perform a surgical operation while observing a state in the body cavity of the patient 5 on the 3D monitor 12.

The data transmission unit 33 transmits the endoscope image data Id input from the image combining unit 32 to the instruction-side device 3.

In the instruction-side device 3, the image combining unit 43 receives the endoscope image data Id from the operation-side device 2 (the data transmission unit 33).

When the 3D image data Pd2 is not input from the image generation unit 42, the image combining unit 43 outputs the endoscope image data Id to the 3D monitor 21.

The 3D monitor 21 displays the endoscope image 50 based on the endoscope image data Id (see FIG. 2). This enables the instructor 6 to have a common viewpoint with the surgical operator 4 in the surgery room Rm1 while staying in the instruction room Rm2, and to observe the state in the body cavity of the patient 5 and the situation of the surgical operation by the surgical operator 4.

Then, the instructor 6 moves his/her hand within a detection range of the three-dimensional position detecting unit 22 while confirming the endoscope image 50 on the 3D monitor 21. At this time, the three-dimensional position detecting unit 22 detects the hand position of the instructor 6, and outputs the position information PI to the image generation unit 42.

When the position information PI is input from the three-dimensional position detecting unit 22 to the image generation unit 42, the image generation unit 42 generates the three-dimensional hand model image 51 (see FIG. 3) based on the input position information PI.

Figure 9:
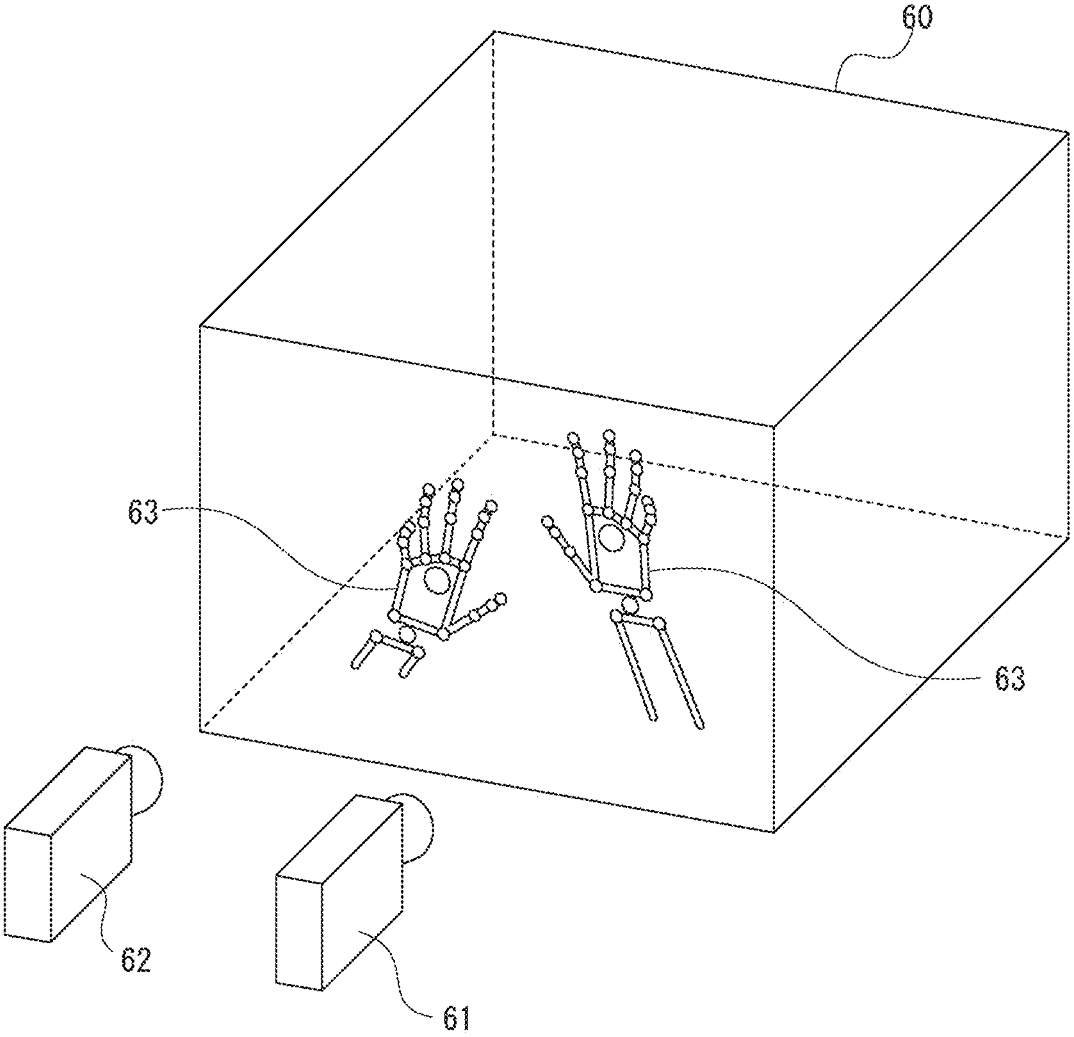
FIG. 9 is a drawing for describing a three-dimensional virtual space when a three-dimensional hand model image is generated, according to an embodiment.

FIG. 9 is a drawing for describing a three-dimensional virtual space when the three-dimensional hand model image

Figure 10:
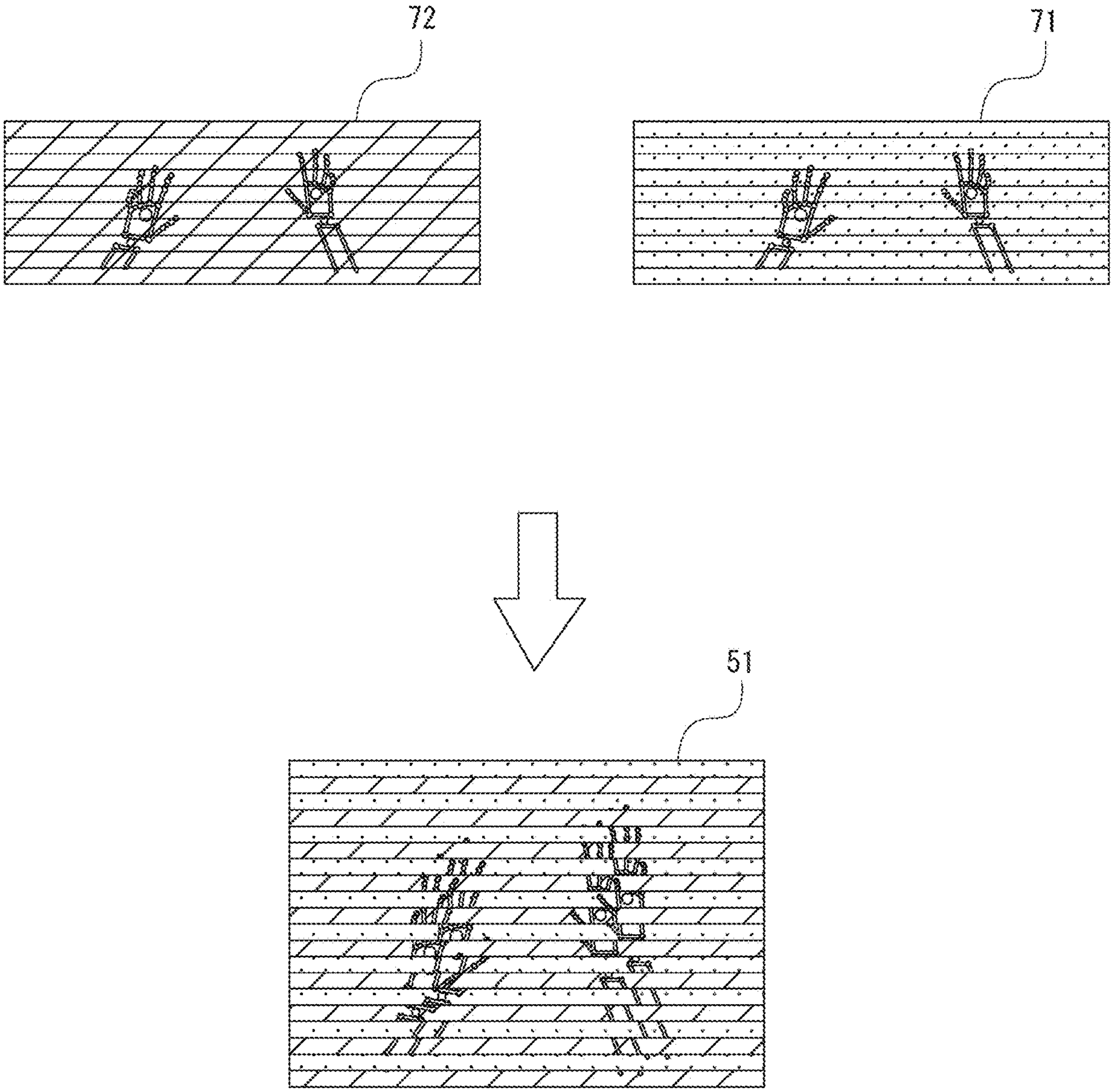
FIG. 10 is a drawing for describing a method for generating the three-dimensional hand model image, according to an embodiment.

51 is generated, according to an embodiment. FIG. 10 is a drawing for describing a method for generating the three-dimensional hand model image 51, according to an embodiment.

The image generation unit 42 locates hand models 63 (polygons) imitating the hands of the instructor 6 in a three-dimensional virtual space 60 as illustrated in FIG. 9 based on the position information PI input from the three-dimensional position detecting unit 22. With respect to the three-dimensional virtual space 60, a right eye virtual camera 61 is disposed at a position corresponding to the right eye, and a left eye virtual camera 62 is disposed at a position corresponding to the left eye.

Then, the image generation unit 42 obtains an image of the three-dimensional virtual space 60 captured by the right eye virtual camera 61 and the left eye virtual camera 62 to generate each of a right eye virtual image 71 and a left eye virtual image 72 as illustrated in the upper side of FIG. 10. For easy distinction between the right eye virtual image 71 and the left eye virtual image 72, patterns (hatching, dots, and the like) are entirely drawn in FIG. 10, but these patterns actually are not in the right eye virtual image 71 or the left eye virtual image 72.

The right eye virtual image 71 and the left eye virtual image 72 have the same number of pixels in the horizontal direction as the number of pixels of the 3D monitor 21, and have the number of pixels in the perpendicular direction half the number of pixels of the 3D monitor 21.

When the right eye virtual image 71 and the left eye virtual image 72 are generated, the image generation unit 42 generates the hand model image 51 in which the right eye virtual image 71 and the left eye virtual image 72 are alternately arranged for each horizontal line as illustrated in the lower side of FIG. 10. That is, the image generation unit 42 generates the three-dimensional hand model image 51 by the line-by-line method.

Then, the image generation unit 42 outputs the 3D image data Pd2 of the hand model image 51 to the image combining unit 43.

As described above, the 3D monitor 21 includes different polarization filters alternately stacked on odd-numbered lines and even-numbered lines, and is a monitor that can display a 3D image by what is called a line-by-line method.

Accordingly, since the hand model image 51 is displayed on the 3D monitor 21 based on the 3D image data Pd2, the instructor 6 wearing the polarized glasses 7 can see only the right eye virtual image 71 by the right eye, and can see only the left eye virtual image 72 by the left eye. Then, the right eye virtual image 71 and the left eye virtual image 72 are images virtually captured in the three-dimensional virtual space 60 by the right eye virtual camera 61 and the left eye virtual camera 62 disposed to be separated in the horizontal direction, respectively, thus providing what is called parallax images.

Therefore, the instructor 6 sees the right eye virtual image 71 by the right eye and sees the left eye virtual image 72 by the left eye, thereby being able to three-dimensionally see the hand model image 51.

The image combining unit 43 generates the combined image 53 in which the hand model image 51 based on the 3D image data Pd2 supplied from the image generation unit 42 is superimposed on the endoscope image 50 based on the endoscope image data Id received from the operation-side device 2 (the data transmission unit 33). Then, the image combining unit 43 outputs the instruction-side combined image data Cd2 of the generated combined image 53 to the 3D monitor 21.

Accordingly, the 3D monitor 21 displays the combined image 53 based on the instruction-side combined image data Cd2 input from the image combining unit 43. This enables the instructor 6 to three-dimensionally confirm his/her own hand position (move) on the endoscope image 50.

Then, when the instructor 6 inputs instruction contents by a predetermined move (gesture) of the hand while confirming the combined image 53, the three-dimensional position detecting unit 22 detects the predetermined move as the instruction contents. Then, the three-dimensional position detecting unit 22 outputs the instruction content information CI indicating the detected instruction contents to the data transmission unit 41 and the image generation unit 42.

When the position information PI and the instruction content information CI are input from the three-dimensional position detecting unit 22 to the image generation unit 42, the image generation unit 42 generates the three-dimensional hand model image 51 and annotation image 52 (see FIG. 4) based on the position information PI and the instruction content information CI input from the three-dimensional position detecting unit 22.

Figure 11:
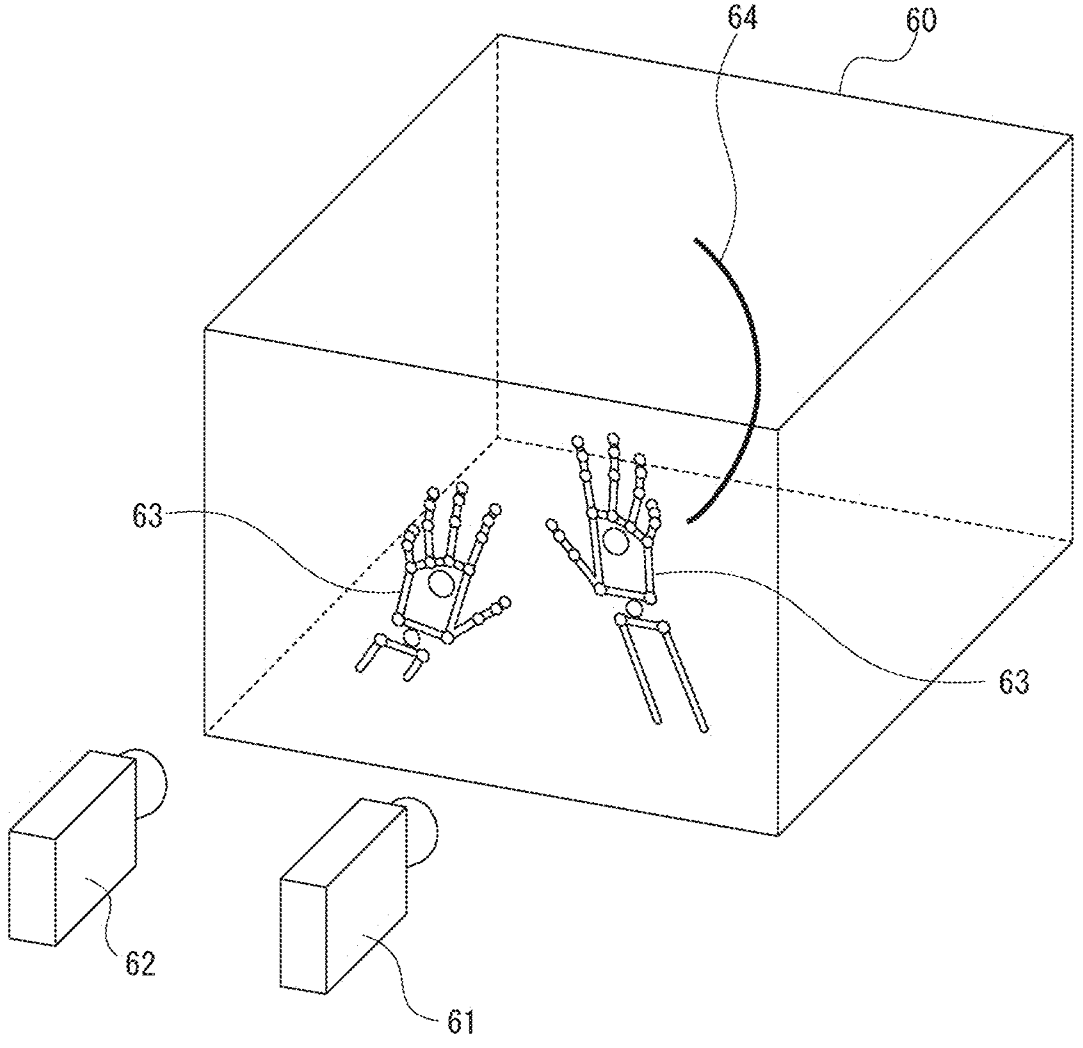
FIG. 11 is a drawing for describing a three-dimensional virtual space when the three-dimensional hand model image and a three-dimensional annotation image are generated, according to an embodiment.
Figure 12:
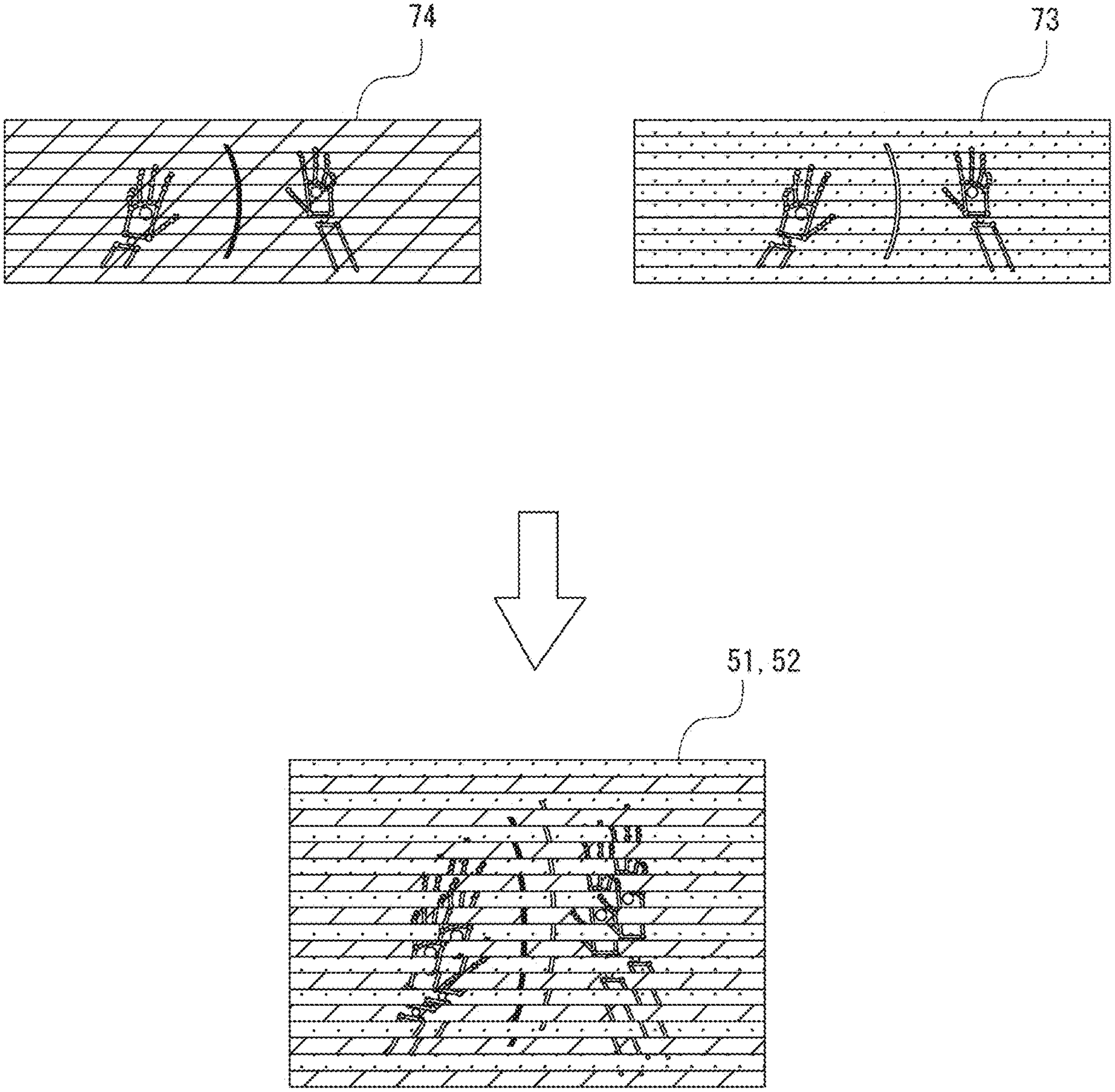
FIG. 12 is a drawing for describing a method for generating the three-dimensional hand model image and annotation image, according to an embodiment.

FIG. 11 is a drawing for describing a three-dimensional virtual space when the three-dimensional hand model image 51 and annotation image 52 are generated, according to an embodiment. FIG. 12 is a drawing for describing a method for generating the three-dimensional hand model image 51 and annotation image 52, according to an embodiment. Since the parts overlapping with FIG. 9 and FIG. 10 are similar, the descriptions are omitted for conciseness.

As illustrated in FIG. 11, the image generation unit 42 locates the hand models 63 based on the position information PI, and locates an instruction content model 64 (a polygon) indicating instruction contents based on the instruction content information CI in the three-dimensional virtual space 60.

Then, the image generation unit 42 obtains an image of the three-dimensional virtual space 60 captured by the right eye virtual camera 61 and the left eye virtual camera 62 to obtain each of a right eye virtual image 73 and a left eye virtual image 74 as illustrated in the upper side of FIG. 12.

When the right eye virtual image 73 and the left eye virtual image 74 are generated, the image generation unit 42 generates the hand model image 51 and the annotation image 52 in which the right eye virtual image 73 and the left eye virtual image 74 are alternately arranged for each horizontal line as illustrated in the lower side of FIG. 12. That is, the image generation unit 42 generates the three-dimensional hand model image 51 and annotation image 52 by the line-by-line method.

Then, the image generation unit 42 outputs the 3D image data Pd2 of the hand model image 51 and the annotation image 52 to the image combining unit 43.

The image combining unit 43 generates the combined image 54 in which the hand model image 51 and the annotation image 52 based on the 3D image data Pd2 input from the image generation unit 42 are superimposed on the endoscope image 50 based on the endoscope image data Id received from the operation-side device 2 (the data transmission unit 33). Then, the image combining unit 43 outputs the instruction-side combined image data Cd2 of the generated combined image 54 to the 3D monitor 21.

Accordingly, the 3D monitor 21 displays the combined image 54 based on the instruction-side combined image data Cd2 input from the image combining unit 43. This enables the instructor 6 to three-dimensionally confirm the instruction contents input by the predetermined move (gesture) of his/her own hand.

Here, the image generation unit 42 generates the hand model image 51 and the annotation image 52 using a shader process of the GPU 26. Therefore, the instruction-side device 3 can display the combined images 53, 54 on the 3D monitor 21 at, for example, 60 Hz, and a delay time until the display of the combined images 53, 54 is extremely short. That is, the 3D monitor 21 displays the combined images 53, 54 with a short time lag.

This enables the instructor 6 to three-dimensionally confirm his/her own hand position and the instruction contents (operation input) without feeling the time lag.

The data transmission unit 41 transmits the instruction content information CI input from the three-dimensional position detecting unit 22 to the operation-side device 2. In the transmission to the operation-side device 2, since the instruction content information CI having a smaller communication capacity than the 3D image data Pd2 generated by the image generation unit 42 is transmitted, a communication delay in data transmission from the instruction-side device 3 to the operation-side device 2 is reduced.

In the operation-side device 2, the image generation unit 31 receives the instruction content information CI from the instruction-side device 3 (the data transmission unit 41). The image generation unit 31 generates the three-dimensional annotation image 52 (see FIG. 5) based on the received instruction content information CI.

Figure 13:
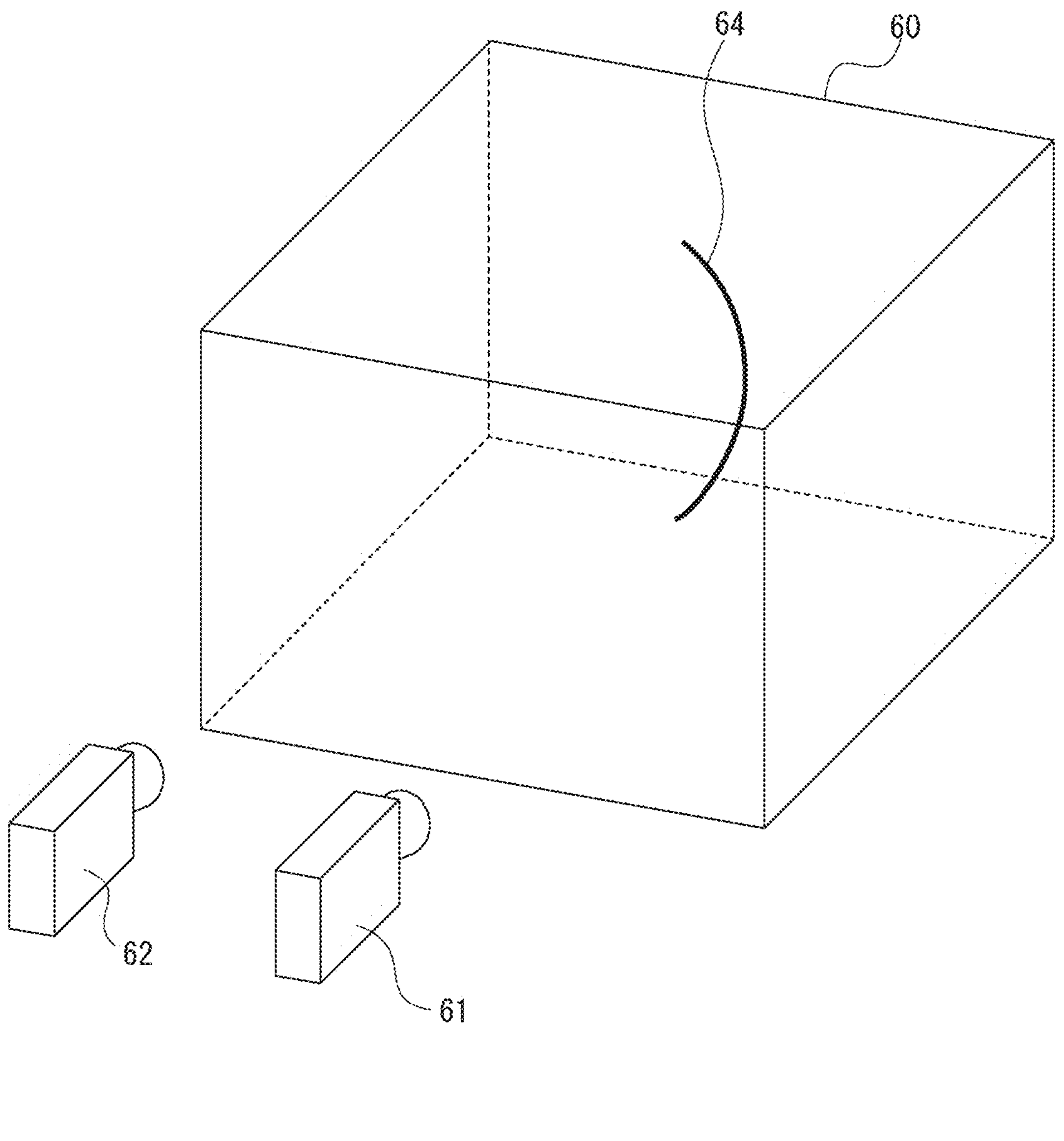
FIG. 13 is a drawing for describing a three-dimensional virtual space when the three-dimensional annotation image is generated, according to an embodiment.
Figure 14:
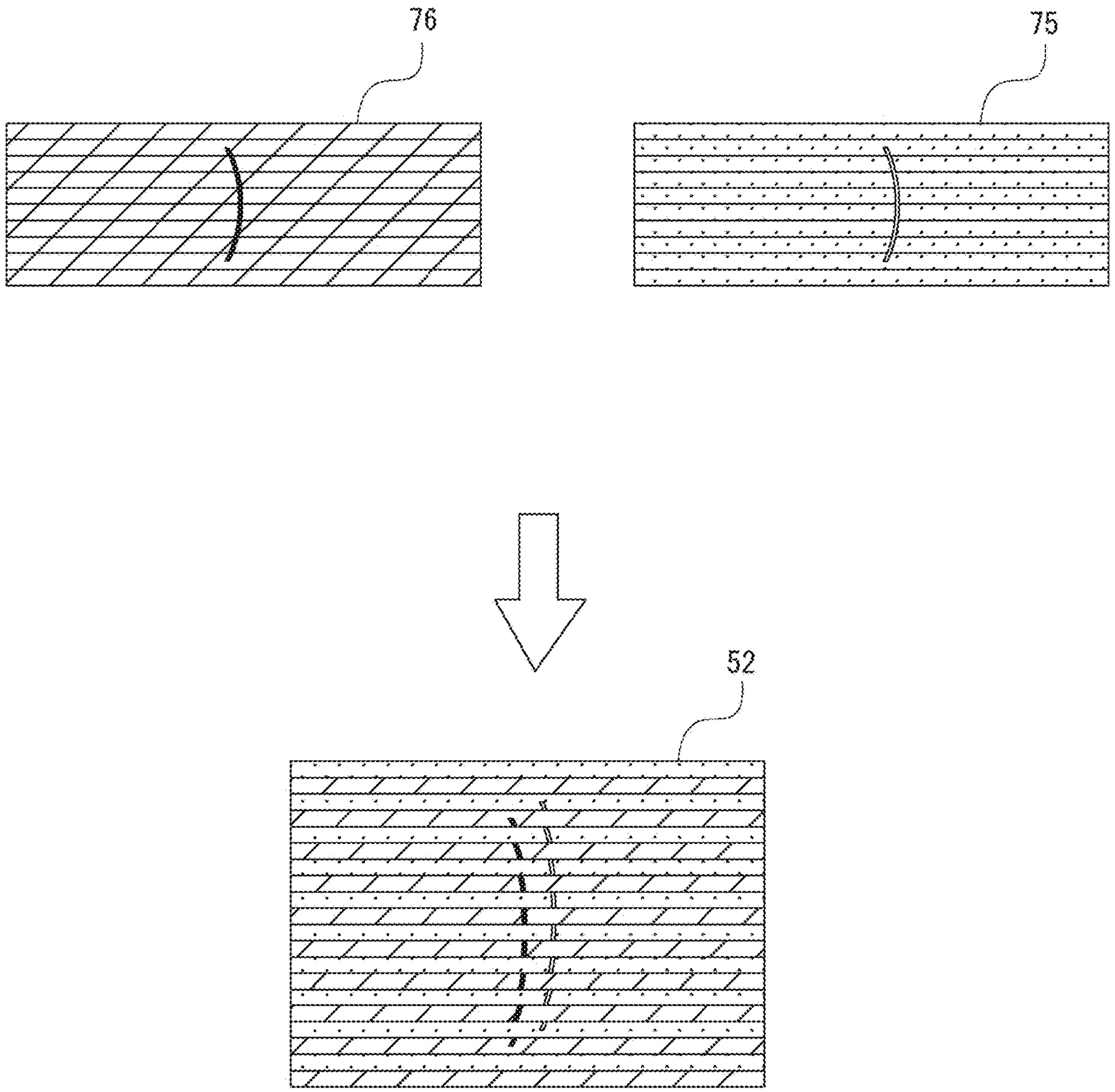
FIG. 14 is a drawing for describing a method for generating the three-dimensional annotation image, according to an embodiment.

FIG. 13 is a drawing for describing a three-dimensional virtual space when the three-dimensional annotation image 52 is generated, according to an embodiment. FIG. 14 is a drawing for describing a method for generating the three-dimensional annotation image 52, according to an embodiment. Since the parts overlapping with FIG. 9 to FIG. 12 are similar, the descriptions are omitted for conciseness.

The image generation unit 31 locates the instruction content model 64 based on the instruction content information CI received from the instruction-side device 3 in the three-dimensional virtual space 60 as illustrated in FIG. 13.

Then, the image generation unit 31 obtains an image of the three-dimensional virtual space 60 captured by the right eye virtual camera 61 and the left eye virtual camera 62 to obtain each of a right eye virtual image 75 and a left eye virtual image 76 as illustrated in the upper side of FIG. 14.

When the right eye virtual image 75 and the left eye virtual image 76 are generated, the image generation unit 31 generates the annotation image 52 in which the right eye virtual image 75 and the left eye virtual image 76 are alternately arranged for each horizontal line as illustrated in the lower side of FIG. 14. That is, the image generation unit 31 generates the three-dimensional annotation image 52 by the line-by-line method.

Then, the image generation unit 31 outputs the 3D image data Pd1 of the annotation image 52 to the image combining unit 32.

The image combining unit 32 generates the combined image 55 in which the annotation image 52 based on the 3D image data Pd1 input from the image generation unit 31 is superimposed on (combined with) the endoscope image 50 based on the endoscope image data Id input from the endoscope 11. Then, the image combining unit 32 outputs the operation-side combined image data Cd1 of the generated combined image 55 to the 3D monitor 12 and the data transmission unit 33.

Accordingly, the 3D monitor 12 displays the combined image 55 based on the operation-side combined image data Cd1 input from the image combining unit 32. This enables the surgical operator 4 to three-dimensionally confirm the instruction contents of the instructor 6.

Here, the image generation unit 31 generates the annotation image 52 using a shader process of the GPU 16. Therefore, the operation-side device 2 can display the combined image 55 on the 3D monitor 12 at, for example, 60 Hz, and a delay time until the display of the combined image 55 is extremely short. That is, the 3D monitor 12 displays the combined image 55 with a short time lag.

This enables the surgical operator 4 in the surgery room Rm1 to perform the surgical operation on the patient 5 while confirming the instruction contents of the instructor 6 in the instruction room Rm2 on the 3D monitor 12 without feeling the time lag.

The data transmission unit 33 transmits the operation-side combined image data Cd1 input from the image combining unit 32 to the instruction-side device 3.

Figure 15:
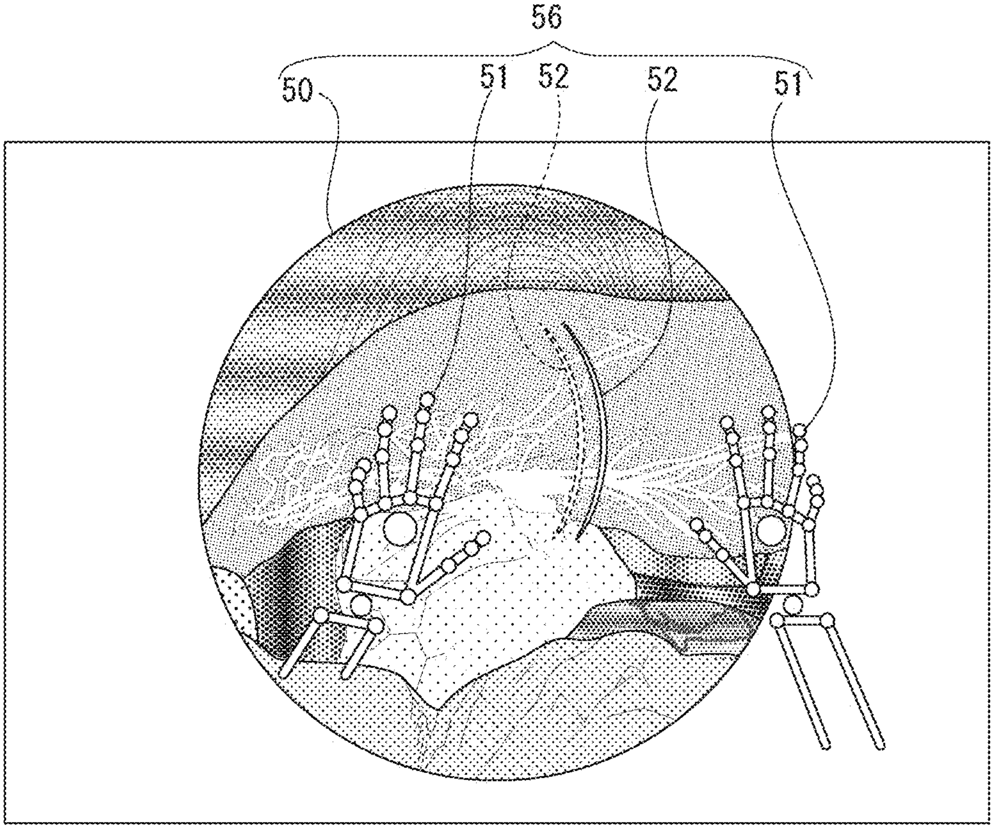
FIG. 15 is a drawing illustrating a combined image in which a hand model image and an annotation image based on 3D image data are superimposed on a combined image based on operation-side combined image data, according to an embodiment.

FIG. 15 is a drawing illustrating a combined image 56 in which the hand model image 51 and the annotation image 52 based on the 3D image data Pd2 are superimposed on the combined image 55 based on the operation-side combined image data Cd1, according to an embodiment.

When the operation-side combined image data Cd1 is received from the operation-side device 2 (the data transmission unit 33), as illustrated in FIG. 15, the image combining unit 43 generates the combined image 56 in which the hand model image 51 and the annotation image 52 based on the 3D image data Pd2 input from the image generation unit 42 are superimposed on the combined image 55 (the endoscope image 50 and the annotation image 52) based on the operation-side combined image data Cd1. Then, the image combining unit 43 outputs the instruction-side combined image data Cd2 of the generated combined image 56 to the 3D monitor 21. The 3D monitor 21 displays the combined image 56 based on the generated instruction-side combined image data Cd2.

This enables the instructor 6 to three-dimensionally confirm whether or not the annotation images 52 displayed based on the respective operation-side combined image data Cd1 and 3D image data Pd2 are displaced from one another on the 3D monitor 21.

When the displacement is generated, the instructor 6 can confirm, for example, the displacement between the annotation images 52 as illustrated in FIG. 15 on the 3D monitor 21.

Here, in consideration of the confirmation of display contents, the image generation unit 42 may generate the combined image 56 so as to have the annotation image 52 based on the 3D image data Pd2 in a display format different from that of the annotation image 52 based on the operation-side combined image data Cd1 (the 3D image data Pd1).

For example, as illustrated in FIG. 15, by displaying with a dashed line, the annotation image 52 based on the 3D image data Pd2 can be displayed on the 3D monitor 21 to be distinguished from the display (a solid line) of the annotation image 52 based on the operation-side combined image data Cd1 (the 3D image data Pd1).

As described above, both the annotation image 52 based on the operation-side combined image data Cd1 (the 3D image data Pd1) and the annotation image 52 based on the 3D image data Pd2 are displayed to enable the confirmation, and this has a meaning as follows.

For example, the instruction content information CI transmitted from the instruction-side device 3 may possibly be partially lost when received by the operation-side device 2 due to a communication failure or the like. In some embodiments, unadjusted setting between the respective devices (2, 3), unadjusted difference in resolution between the 3D monitors 12, 21, or the like may possibly cause the displacement of the display coordinate of the annotation image 52 and the like.

In this case, the 3D monitor 21 displays the image as illustrated in FIG. 15 due to the displacement of the display coordinate in some cases.

When the instruction content information CI is partially lost, while the image generation unit 31 of the operation-side device 2 generates the annotation image 52 as illustrated in FIG. 5 based on the received instruction content information CI in ordinary circumstances, the loss of a part of the instruction content information CI generates 3D image data Pd1 indicating only a part of the annotation image 52 (hereinafter also noted as deficient 3D image data Pd1) in some cases.

At this time, in the image combining unit 32, the annotation image 52 based on the deficient 3D image data Pd1 is combined with the endoscope image 50 based on the endoscope image data Id, and the combined image 55 in which only a part of the annotation image 52 is superimposed on the endoscope image 50 is generated.

Therefore, the 3D monitor 12 displays the combined image 55 in which a part of the annotation image 52 is lost. In this state, the instruction contents of the instructor 6 are not accurately reflected on the 3D monitor 12, and the surgical operator 4 performs the surgical operation in a state where the surgical operator 4 cannot grasp all of the instruction contents of the instructor 6.

Meanwhile, the instruction-side device 3 combines the combined image 55 based on the operation-side combined image data Cd1 received from the operation-side device 2 with the annotation image 52 based on the 3D image data Pd2 input from the image generation unit 42. At this time, when the annotation image 52 based on the operation-side combined image data Cd1 (the deficient 3D image data Pd1) completely overlaps with the annotation image 52 based on the 3D image data Pd2, the instructor 6 possibly cannot confirm the loss of the annotation image 52 in the display of the 3D monitor 12 of the operation-side device 2.

In order for the instructor 6 to confirm the display situation of the 3D monitor 12 in the surgical operator 4 side, it is preferred to display the images based on the 3D image data Pd1, Pd2 in different formats.

Therefore, the image generation unit 42 generates the annotation image 52 indicated by the dashed line based on the instruction content information CI.

This enables the instructor 6 to confirm that the part of the annotation image 52 indicated by only the dashed line is not displayed on the 3D monitor 12 of the operation-side device 2.

That is, the instructor 6 can easily compare his/her own instruction contents with the display contents of the 3D monitor 12 that the surgical operator 4 sees on the 3D monitor 21.

As described above, the instructor 6 can see both of the images based on the 3D image data Pd1, Pd2 by seeing the combined image 56 based on the instruction-side combined image data Cd2, thereby confirming whether or not his/her own instruction contents are accurately transmitted to the surgical operator 4. When it can be recognized that the instructions by the image are not accurately transmitted, the instructor 6 can take various measures.

As an example of the display format for distinguishing between the annotation image 52 based on the operation-side combined image data Cd1 (the 3D image data Pd1) and the annotation image 52 based on the 3D image data Pd2, the distinction using the dashed line and the solid line is described. However, the display format is not limited thereto insofar as the 3D image data Pd1, Pd2 is distinguishable, and the distinction can be performed by making the line type, such as a line width, the color, the luminance, and the like different. The distinction can also be performed by highlighting any of the 3D image data Pd1, Pd2.

Further, it is considered to distinguish and display the parts where the annotation image 52 based on the operation-side combined image data Cd1 (the 3D image data Pd1) is not matched to the annotation image 52 based on the 3D image data Pd2.

The image generation unit 31 and the image generation unit 42 can adjust the parallax of the three-dimensional hand model image 51 and annotation image 52 by capturing an image with the right eye virtual camera 61 or the left eye virtual camera 62 at a position displaced in the horizontal direction.

Figure 16:
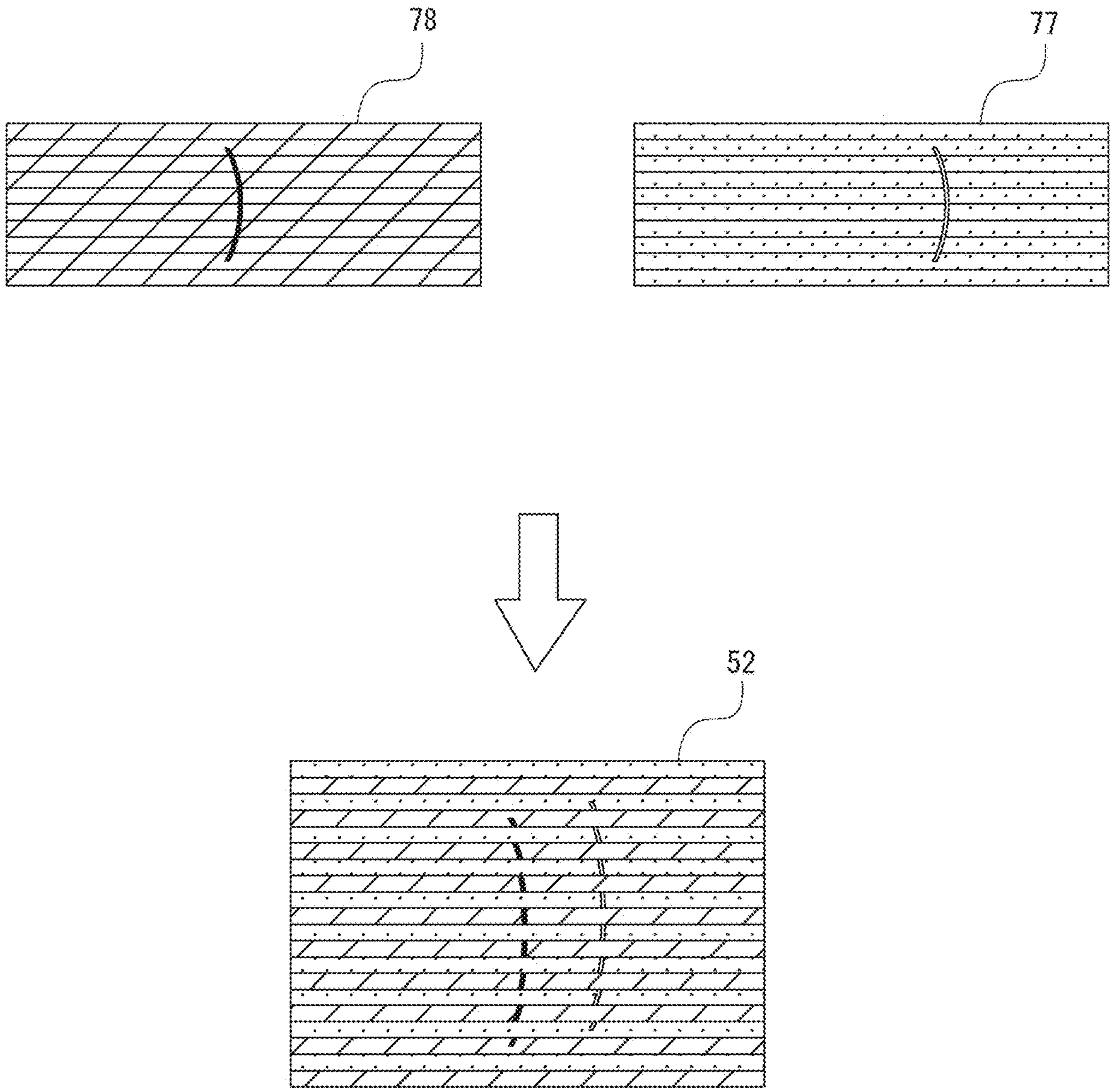
FIG. 16 is a drawing for describing a method for generating a three-dimensional annotation image when a parallax is adjusted, according to an embodiment.

For example, when a predetermined operation is input to an operation unit (not illustrated) by the surgical operator 4, the image generation unit 31 moves the right eye virtual camera 61 and the left eye virtual camera 62 so as to be separated from one another to capture a right eye virtual image 77 and a left eye virtual image 78 as illustrated in the upper side of FIG. 16. Then, the image generation unit 31 generates the annotation image 52 as illustrated in the lower side of FIG. 16 based on the right eye virtual image 77 and the left eye virtual image 78.

Thus, when the annotation image 52 as illustrated in the lower side of FIG. 16 is displayed on the 3D monitor 12, a focal length of the annotation image 52 becomes long, and the three-dimensional annotation image 52 distantly appears.

As described above, the image generation unit 31 and the image generation unit 42 can adjust the parallax of the hand model image 51 and the annotation image 52 displayed on the 3D monitor 12 and the 3D monitor 21 by displacing the positions in the horizontal direction of the right eye virtual image and the left eye virtual image.

Accordingly, the hand model image 51 and the annotation image 52 can be located at three-dimensionally appropriate positions on the endoscope image 50.

Figure 17:
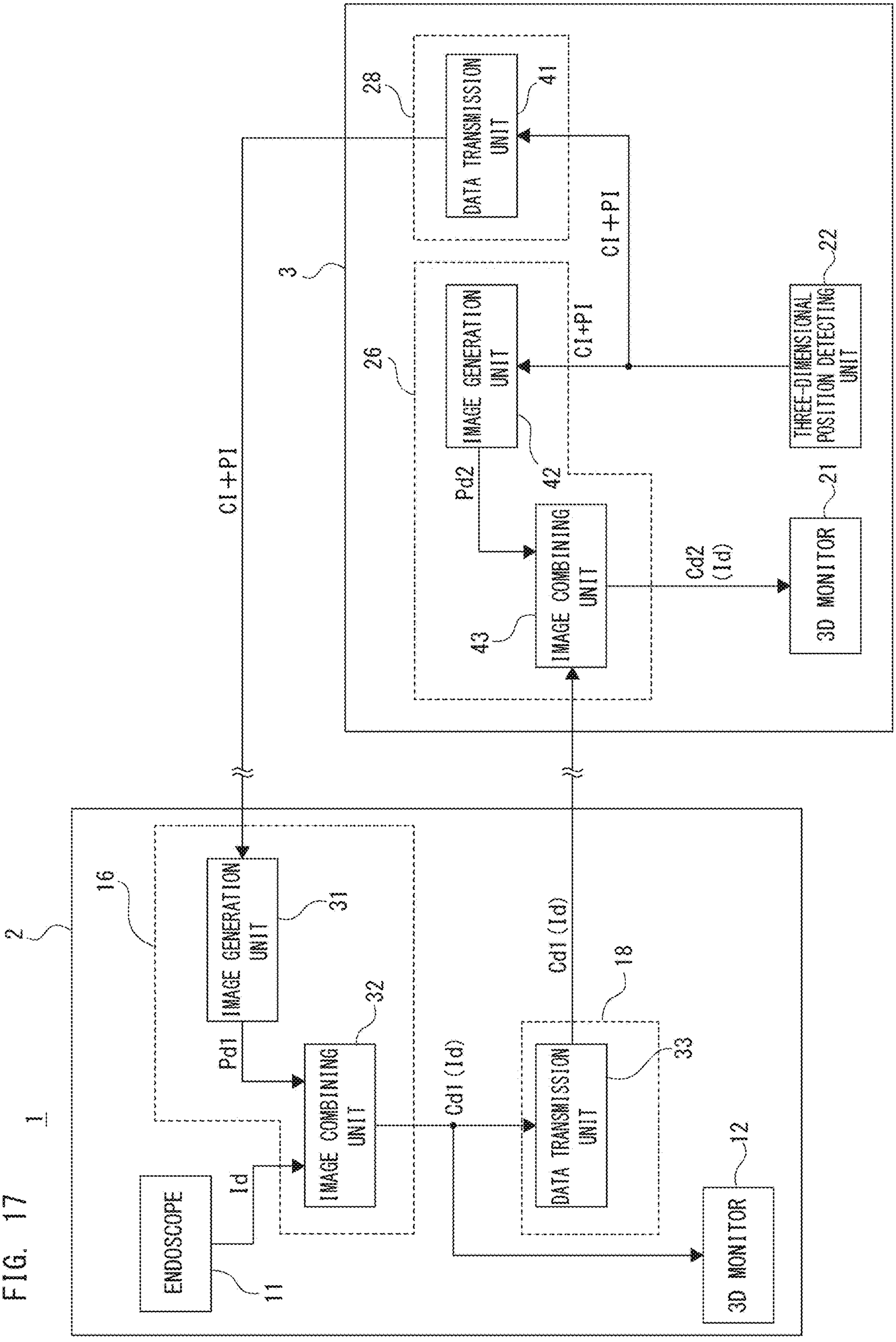
FIG. 17 is a drawing for describing a functional configuration and a flow of data in an assistance system, according to an embodiment.

FIG. 17 is a drawing for describing a functional configuration and a flow of data in the assistance system 1, according to an embodiment. An assistance system 1 of FIG. 17 is different from the assistance system 1 described above in that the 3D monitor 12 of the operation-side device 2 displays the hand model image 51. When the position information PI is detected by the three-dimensional position detecting unit 22, the position information PI is output to the image generation unit 42 and the data transmission unit 41. Then, the data transmission unit 41 transmits the position information PI to the operation-side device 2 together with the instruction content information CI.

When the position information PI is received, the image generation unit 31 of the operation-side device 2 locates the hand models 63 based on the position information PI in the three-dimensional virtual space 60 (see FIG. 9) similarly to the image generation unit 42.

Then, the image generation unit 31 obtains an image of the three-dimensional virtual space 60 captured by the right eye virtual camera 61 and the left eye virtual camera 62 to obtain each of the right eye virtual image 71 and the left eye virtual image 72 as illustrated in the upper side of FIG. 10.

When the right eye virtual image 71 and the left eye virtual image 72 are generated, the image generation unit 31 generates the three-dimensional hand model image 51 in which the right eye virtual image 71 and the left eye virtual image 72 are alternately arranged for each horizontal line as illustrated in the lower side of FIG. 10. Then, the image generation unit 31 outputs the 3D image data Pd1 of the hand model image 51 to the image combining unit 32.

The image combining unit 32 generates the combined image 53 (see FIG. 3) in which the hand model image 51 based on the 3D image data Pd1 input from the image generation unit 31 is superimposed on the endoscope image 50 based on the endoscope image data Id input from the endoscope 11, and outputs the operation-side combined image data Cd1 of the combined image 53 to the 3D monitor 12. Accordingly, the 3D monitor 12 displays the combined image 53 based on the operation-side combined image data Cd1.

This enables the surgical operator 4 to three-dimensionally confirm the actual hand position (move) of the instructor 6.

When the position information PI and the instruction content information CI are received, similarly to the image generation unit 42, the image generation unit 31 of the operation-side device 2 locates the hand models 63 based on the position information PI, and locates the instruction content model 64 based on the instruction content information CI in the three-dimensional virtual space 60 (see FIG. 11).

Then, the image generation unit 31 obtains an image of the three-dimensional virtual space 60 captured by the right eye virtual camera 61 and the left eye virtual camera 62 to obtain each of the right eye virtual image 73 and the left eye virtual image 74 as illustrated in the upper side of FIG. 12.

When the right eye virtual image 73 and the left eye virtual image 74 are generated, the image generation unit 31 generates the three-dimensional hand model image 51 and annotation image 52 in which the right eye virtual image 73 and the left eye virtual image 74 are alternately arranged for each horizontal line as illustrated in the lower side of FIG. 12. Then, the image generation unit 31 outputs the 3D image data Pd1 of the hand model image 51 and the annotation image 52 to the image combining unit 32.

The image combining unit 32 generates the combined image 54 (see FIG. 4) in which the hand model image 51 and the annotation image 52 based on the 3D image data Pd1 input from the image generation unit 31 is superimposed on the endoscope image 50 based on the endoscope image data Id input from the endoscope 11, and outputs the operation-side combined image data Cd1 of the combined image 54 to the 3D monitor 12. Accordingly, the 3D monitor 12 displays the combined image 54 based on the operation-side combined image data Cd1.

This enables the surgical operator 4 to three-dimensionally confirm the actual hand move of the instructor 6 in addition to the instruction contents of the instructor 6.

As described above, the assistance system 1 includes an assisted device (the operation-side device 2) and an assistance device (the instruction-side device 3) disposed to be separated from the assisted device (the operation-side device 2).

The assistance device (the instruction-side device 3) includes the three-dimensional position detecting unit 22 that three-dimensionally detects the hand position of the instructor 6, and the data transmission unit 41 that transmits the position information PI indicating the hand position detected by the three-dimensional position detecting unit 22.

The assisted device (the operation-side device 2) includes a first image generation unit (the image generation unit 31) that generates the three-dimensional hand model image 51 imitating the hand of the instructor 6 based on the transmitted position information PI, and a first image combining unit (the image combining unit 32) that combines the hand model image 51 with a captured image (the endoscope image 50) taken by the assisted device (the operation-side device 2) to generate a first combined image (the combined image 53).

This configuration and operation enables the operation-side device 2 to display the combined image 53 in which the three-dimensional hand model image 51 imitating the hand of the instructor 6 is superimposed on the endoscope image 50 on the 3D monitor 12.

Accordingly, the surgical operator 4 visually confirming the 3D monitor 12 through the polarized glasses 7 visually confirms the three-dimensional hand model image 51, thereby being able to three-dimensionally confirm the actual hand position (move) of the instructor 6 from the same viewpoint. That is, in the assistance system 1, the instruction contents of the instructor 6 can be recognized with more accuracy.

The three-dimensional position detecting unit 22 detects the instruction contents of the instructor 6 based on the hand position of the instructor 6, and the data transmission unit 41 transmits the position information PI and the instruction content information CI indicating the instruction contents.

The first image generation unit (the image generation unit 31) generates the hand model image 51 based on the transmitted position information PI, and generates the three-dimensional annotation image 52 based on the transmitted instruction content information CI.

The first image combining unit (the image combining unit 32) combines the hand model image 51 and the annotation image 52 with the captured image (the endoscope image 50) to generate a second combined image (the combined image 54).

Accordingly, the surgical operator 4 visually confirming the 3D monitor 12 through the polarized glasses 7 can three-dimensionally confirm the hand position and the instruction contents of the instructor 6 on the endoscope image 50. That is, in the assistance system 1, the instruction contents of the instructor 6 can be recognized with more accuracy.

The assistance device (the instruction-side device 3) includes a second image generation unit (the image generation unit 42) that generates the hand model image 51 based on the position information PI detected by the three-dimensional position detecting unit 22, and a second image combining unit (the image combining unit 43) that combines the hand model image 51 with the captured image (the endoscope image 50) transmitted from the assisted device (the operation-side device 2) to generate the first combined image (the combined image 53).

Accordingly, the instructor 6 visually confirming the 3D monitor 21 through the polarized glasses 7 can three-dimensionally confirm his/her own hand position on the endoscope image 50.

The second image generation unit (the image generation unit 42) generates the three-dimensional hand model image 51 and annotation image 52 based on the position information PI and the instruction content information CI, and the second image combining unit (the image combining unit 43) combines the hand model image 51 and the annotation image 52 with the captured image (the endoscope image 50) to generate the second combined image (the combined image 54).

Accordingly, the instructor 6 visually confirming the 3D monitor 21 through the polarized glasses 7 can three-dimensionally confirm his/her own hand position and instruction contents on the endoscope image 50.

The first image generation unit (the image generation unit 31) generates a right eye hand model image (the right eye virtual image 71) and a left eye hand model image (the left eye virtual image 72) based on the position information PI using the shader process of the GPU 16, and combines the right eye hand model image (the right eye virtual image 71) and the left eye hand model image (the left eye virtual image 72) by the line-by-line method to generate the hand model image 51.

Accordingly, in the operation-side device 2, a delay time until the combined image 53 is displayed on the 3D monitor 12 can be extremely shortened, and the display can be performed with a short time lag.

The first image generation unit (the image generation unit 31) adjusts the parallax of the three-dimensional hand model image 51 by displacing the positions in the horizontal direction of the right eye hand model image (the right eye virtual image 71) and the left eye hand model image (the left eye virtual image 72).

Accordingly, in the operation-side device 2, when the hand model image 51 is seen to be displaced in the depth direction with respect to the endoscope image 50 by the surgical operator 4, by performing the parallax adjustment, the position in the depth direction of the hand model image 51 with respect to the endoscope image 50 can be adjusted. Thus, in the operation-side device 2, the hand move of the instructor 6 can be recognized with more accuracy.

2. Additional Embodiments

In some embodiments, as an example of the assistance system 1, the surgery assistance system that enables the surgical operator 4 to perform the surgical operation on the patient 5 while receiving the instructions of the instructor 6 at a remote location has been described. However, the assistance system 1 is widely applicable to the situation in which the instructor 6 at the remote location gives the instructions to the surgical operator 4 while visually confirming the captured image in the operation side.

For example, the assistance system 1 can be applied to various uses, such as athletes and head coaches in sports instruction, instructors and students in learning assistance including education and vocational training, and presenters and listeners in remote conferences.

In the above-described embodiments, while the example in which the endoscope 11 captures the image as illustrated in FIG. 1 has been described, an image capturing device is one that can capture an image of the surgical operation on the surgical operator 4 side, and the image capturing device is not limited to the endoscope 11.

While, as an example of the three-dimensional position detecting unit 22 illustrated in FIG. 1, the hand position of the instructor 6 is detected by the stereo infrared camera in the above-described embodiment, another device may be used for the detection insofar as the hand position and the instruction contents of the instructor 6 can be three-dimensionally detected.

While the GPU 16 is configured to function as the image generation unit 31 and the image combining unit 32 in the above-described embodiment, the CPU 13 may be configured to function as the image generation unit 31 and the image combining unit 32, or the functions of the image generation unit 31 and the image combining unit 32 may be assigned to the CPU 13 and the GPU 16.

While the GPU 26 is configured to function as the image generation unit 42 and the image combining unit 43 in the above-described embodiment, the CPU 23 may be configured to function as the image generation unit 42 and the image combining unit 43, or the functions of the image generation unit 42 and the image combining unit 43 may be assigned to the CPU 23 and the GPU 26.

While the 3D images displayed on the 3D monitor 12 and the 3D monitor 21 are generated by the line-by-line method in the above-described embodiment, the 3D images may be generated by another method. That is, insofar as at least the hand model image 51 and the annotation image 52 are three-dimensionally displayed on the 3D monitor 12 and the 3D monitor 21, any method may be used.

With various embodiments of the present disclosure, the instructor at the remote location can appropriately assist the surgical operator.

Finally, the embodiments described above are merely examples, and the technology of the present disclosure is not limited to the above-described embodiments. All combinations of the configurations described in the embodiments are not necessarily required for solving the problem. Furthermore, the effects described in the present disclosure are merely examples and not limited, and other effects may be achieved, or a part of the effects described in the present disclosure may be achieved.

We claim:

1. An assistance system comprising:
- an assisted device; and
- an assistance device disposed to be separated from the assisted device, wherein:
- the assistance device includes a first storage that stores one or more first programs and a first central processing unit (CPU), and the first CPU accesses the first storage and executes the one or more first programs to cause the first CPU to implement:
  - a three-dimensional position detecting unit that three-dimensionally detects a hand position of an instructor; and
  - a data transmission unit that transmits position information indicating the hand position detected by the three-dimensional position detecting unit, and
- the assisted device includes a second storage that stores one or more second programs and a second central processing unit (CPU), and the second CPU accesses the first storage and execute the one or more second programs to cause the second CPU to implement:
  - a first image generation unit that generates a hand model image in three dimensions that imitates a hand of the instructor based on the transmitted position information; and
  - a first image combining unit that combines the hand model image with a captured image of a body cavity of a patient during a surgical operation taken by the assisted device to generate a first combined image,
- wherein the assistance device displays an annotation image based on instruction content transmitted to the assisted device in a first display format and an annotation image based on instruction content generated in the assistance device in a second display format different from the first display format.

2. The assistance system according to claim 1, wherein:
- the three-dimensional position detecting unit detects an instruction content of the instructor based on the hand position of the instructor,
- the data transmission unit transmits the position information and instruction content information indicating the instruction content,
- the first image generation unit generates the hand model image based on the transmitted position information, and generates a three-dimensional annotation image based on the transmitted instruction content information, and the first image combining unit combines the hand model image and the three-dimensional annotation image with the captured image to generate a second combined image.

3. The assistance system according to claim 2, wherein:

the first CPU accesses the first storage and executes the one or more first programs to further cause the first CPU to implement:

a second image generation unit that generates the hand model image based on the position information detected by the three-dimensional position detecting unit; and a second image combining unit that combines the hand model image with the captured image transmitted from the assisted device to generate the first combined image.

4. The assistance system according to claim 3, wherein:

the second image generation unit generates the hand model image and the three-dimensional annotation image based on the position information and the instruction content information, and the second image combining unit combines the hand model image and the three-dimensional annotation image with the captured image to generate the second combined image.

5. The assistance system according to claim 4, wherein:

the first image generation unit generates a right eye hand model image and a left eye hand model image based on the position information using a shader process of a graphics processing unit (GPU), and combines the right eye hand model image and the left eye hand model image by a line-by-line method to generate the hand model image.

6. The assistance system according to claim 5, wherein:

the first image generation unit displaces positions in a horizontal direction of the right eye hand model image and the left eye hand model image to perform a parallax adjustment of the hand model image.

7. The assistance system according to claim 1, wherein:

the first CPU accesses the first storage and executes the one or more first programs to further cause the first CPU to implement:

a second image generation unit that generates the hand model image based on the position information detected by the three-dimensional position detecting unit; and a second image combining unit that combines the hand model image with the captured image transmitted from the assisted device to generate the first combined image.

8. The assistance system according to claim 1, wherein:

the first image generation unit generates a right eye hand model image and a left eye hand model image based on the position information using a shader process of a graphics processing unit (GPU), and combines the right eye hand model image and the left eye hand model image by a line-by-line method to generate the hand model image.

9. The assistance system according to claim 1, wherein the captured image is an endoscope image captured by an endoscope inserted into the body cavity of the patient.

10. The assistance system according to claim 1, wherein the assistance device further includes a display that displays a combined image in which an annotation image based on instruction content transmitted to the assisted device and an annotation image based on instruction content generated in the assistance device are superimposed on the captured image transmitted from the assisted device.

11. The assistance system according to claim 1, wherein the data transmission unit transmits instruction content having a smaller communication capacity than three-dimensional image data generated by the assistance device to reduce a communication delay in data transmission from the assistance device to the assisted device.

12. The assistance system according to claim 1, wherein the assisted device includes a 3D monitor having polarization filters with different polarization directions alternately stacked on odd-numbered lines and even-numbered lines, and the 3D monitor displays the first combined image by a line-by-line method.

13. The assistance system according to claim 1, wherein the three-dimensional position detecting unit includes an infrared irradiation unit and a stereo infrared camera, and photographs a reflected light of an infrared light emitted from the infrared irradiation unit and reflected by the hand of the instructor with the stereo infrared camera to three-dimensionally detect the hand position of the instructor.

14. The assistance system according to claim 1, wherein the first image generation unit generates the hand model image using a shader process of a graphics processing unit (GPU), and the assisted device displays the first combined image with a short time lag.

15. An assistance device disposed to be separated from an assisted device, the assistance device comprising a storage that stores one or more programs and a central processing unit (CPU), and the CPU accesses the storage and executes the one or more programs to cause the CPU to implement:

a three-dimensional position detecting unit that three-dimensionally detects a hand position of an instructor and an instruction content of the instructor with respect to a body cavity of a patient during a surgical operation; and a data transmission unit that transmits position information indicating the hand position detected by the three-dimensional position detecting unit and the instruction content with respect to the body cavity, wherein the assistance device displays an annotation image based on instruction content transmitted to the assisted device in a first display format and an annotation image based on instruction content generated in the assistance device in a second display format different from the first display format.

16. The assistance device according to claim 15, wherein the three-dimensional position detecting unit detects the instruction content based on a gesture in which a tip of a thumb and a tip of a forefinger of the instructor are in contact with each other and detects a trajectory of the tip of the thumb and the tip of the forefinger moving while being in contact with each other as the instruction content.

17. The assistance device according to claim 15, wherein the instruction content includes information on a coordinate, a line type, a color, and a line width specified by an operation input of the instructor.

* * * * *